US012734499B2

(12) United States Patent
Wu et al.

(10) Patent No.: US 12,734,499 B2
(45) Date of Patent: Sep. 15, 2026

(54) LIQUID PLASMA DISCHARGE DEVICE AND METHOD FOR BIODIESEL SYNTHESIS USING SAME

(71) Applicant: REGENTS OF THE UNIVERSITY OF MINNESOTA, Minneapolis, MN (US)

(72) Inventors: Xiao Wu, Moscow, ID (US); Shaobo Deng, Eden Prairie, MN (US); Jun Zhu, Fayetteville, AR (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 18/144,989

(22) Filed: May 9, 2023

(65) Prior Publication Data

US 2023/0271156 A1 Aug. 31, 2023

Related U.S. Application Data

(62) Division of application No. 16/072,774, filed as application No. PCT/US2017/014907 on Jan. 25, 2017, now Pat. No. 11,679,369.

(Continued)

(51) Int. Cl.

*B01J 19/08* (2006.01)
*B01J 8/04* (2006.01)

(Continued)

(52) U.S. Cl.

CPC ........... *B01J 19/088* (2013.01); *B01J 8/0453* (2013.01); *B01J 19/087* (2013.01); *C07C 67/02* (2013.01);

(Continued)

(58) Field of Classification Search

CPC ...... B01J 19/088; B01J 8/0453; B01J 19/087; B01J 2219/0803; B01J 2219/0809;

(Continued)

(56) References Cited

U.S. PATENT DOCUMENTS

2013/0062014 A1* 3/2013 Koo ........................ B23K 10/00 156/345.11
2014/0271354 A1* 9/2014 Tsai .......................... A61L 2/18 422/29

(Continued)

*Primary Examiner* — Xiuyu Tai

(74) *Attorney, Agent, or Firm* — QUARLES & BRADY LLP

(57) ABSTRACT

A process comprises feeding a stream of reactant compounds to a reactor and discharging a liquid plasma into the reactant stream in the reactor, wherein the plasma initiates or accelerates a reaction of the reactant compounds to form a product composition. The reactor can comprise one or more chambers, a high-voltage electrode positioned at a first portion of the one or more chambers, a ground electrode positioned at a second portion of the one or more chambers, and a dielectric plate between the ground electrode and the high-voltage electrode that comprises openings through which the reactant stream can pass from the first portion to the second portion or from the second portion to the first portion. Discharging the plasma can include supplying electrical power to the high-voltage electrode such that plasma is discharged where the reactant stream flows through the openings.

22 Claims, 9 Drawing Sheets

Related U.S. Application Data

(60) Provisional application No. 62/286,715, filed on Jan. 25, 2016.

(51) Int. Cl.
*C07C 67/02* (2006.01)
*C10L 1/02* (2006.01)
*H05H 1/24* (2006.01)

(52) U.S. Cl.
CPC .......... *C10L 1/026* (2013.01); *H05H 1/2406* (2013.01); *B01J 2219/0803* (2013.01); *B01J 2219/0809* (2013.01); *B01J 2219/0811* (2013.01); *B01J 2219/0815* (2013.01); *B01J 2219/0824* (2013.01); *B01J 2219/0828* (2013.01); *B01J 2219/083* (2013.01); *B01J 2219/0869* (2013.01); *B01J 2219/0877* (2013.01); *B01J 2219/0888* (2013.01); *B01J 2219/0892* (2013.01); *B01J 2219/0894* (2013.01); *H05H 1/2443* (2021.05); *H05H 1/246* (2021.05); *H05H 2245/15* (2021.05)

(58) Field of Classification Search
CPC ........ B01J 2219/0811; B01J 2219/0815; B01J 2219/0824; B01J 2219/0828; B01J 2219/083; B01J 2219/0869; B01J 2219/0877; B01J 2219/0888; B01J 2219/0892; B01J 2219/0894; B01J 2219/0813; B01J 2219/0849; B01J 2219/0875; C07C 67/02; C10L 1/026; H05H 1/2406; H05H 1/246; H05H 2245/15; H05H 1/2443; C02F 1/36; C02F 1/722; C02F 1/78; C02F 1/4608; C02F 2303/04; C02F 2101/30; C02F 2305/023; C02F 1/74; C02F 2101/366; C02F 2201/46175; C02F 2201/4618; C02F 2201/4619; C02F 1/4672; C02F 2101/305; C02F 2001/46152; C01B 2201/14; C01B 2201/32; C01B 2201/64; C01B 2201/82; C01B 13/11
See application file for complete search history.

(56) References Cited

U.S. PATENT DOCUMENTS

2015/0139853 A1* 5/2015 Zolezzi-Garreton ........................ C02F 1/4608 422/186.23
2018/0134591 A1* 5/2018 Oinuma .................... C02F 1/36

* cited by examiner

LIQUID PLASMA DISCHARGE DEVICE AND METHOD FOR BIODIESEL SYNTHESIS USING SAME

CROSS-REFERENCE TO RELATED APPLICATION

This application is a division of U.S. Utility application Ser. No. 16/072,774, filed Jul. 25, 2018, which is a United States national phase application under U.S.C. § 371 of International Patent Application No. PCT/US2017/014907, filed Jan. 25, 2017, and published as WO 2017/132242 A1 on Aug. 3, 2017, which claims the benefit of priority to U.S. Provisional Patent Application No. 62/286,715, which was filed Jan. 25, 2016 and entitled "A LIQUID PLASMA DISCHARGE DEVICE AND METHOD FOR BIODIESEL SYNTHESIS USING SAME", which applications are herein incorporated by reference in their entirety for all purposes.

BACKGROUND

As a renewable fuel, biodiesel has become an attractive alternative to petroleum-based diesel fuel. Biodiesel typically burns cleaner than petroleum-based diesel and is formed via mature transesterification technologies that have been in wide use since the 1990s. As a result, large-scale industrial biodiesel production has been highly promoted in the United States of America to address challenges in energy independence, economic prosperity, and environmental sustainability.

Traditionally, vegetable oil and/or animal fats have been the primary feedstock for global biodiesel production. Biodiesel synthesis from vegetable oil/animal fats is a simple catalyst-assisted chemical reaction between triglyceride in the oils or fats (lipids) and alcohol that splits the lipid molecules so that the alcohol can combine with the resulting separated esters to reduce viscosity of the product oil. The general reaction is typically referred to as "transesterification."

The competitiveness of biodiesel to petroleum-based diesel relies primarily on the cost of the biomass feedstock, e.g., of the vegetable oil or animal fats, or both. For example, recently in a typical biodiesel production facility, at least about 70-80% of the cost depends on the price of the biomass feedstock, with the remaining 20-30% depending on the operating costs of the conversion technology. While using recycled waste cooking oils and animal fats can reduce feedstock costs, improving the synthesizing process can be important in achieving cost-effective large-scale production of biodiesel. Conventional methods of producing biodiesel can include so-called "homogeneous" catalytic transesterification involving upstream heating (e.g., to greater than 60° C.), mechanical agitation, long reaction time (e.g., as much as 2 to 4 hours), high-levels of reagents (e.g., alcohols), energy-intensive downstream separation and purification processes, and labor for batch operation. Homogeneous transesterification processes tend to have efficiencies that make it difficult for the resulting biodiesel to be price-competitive with petroleum-based diesel fuel. Moreover, homogeneous transesterification can also be challenging to operate in an environmentally friendly manner.

Extensive research has been conducted to develop more cost-effective and environmental friendly technologies for the conversion of biomass feedstocks such as vegetable oil or animal fats, such as heterogeneous catalytic transesterification, enzymatic catalytic transesterification, and super-critical-methanol transesterification. Mass-transfer limitations caused by diffusion problems between phases have hindered the usefulness and establishment of these technologies.

DESCRIPTION OF THE FIGURES

The drawings, which are not necessarily drawn to scale, illustrate generally, by way of example, but not by way of limitation, various embodiments discussed in the present disclosure.

SUMMARY

Figure 1:
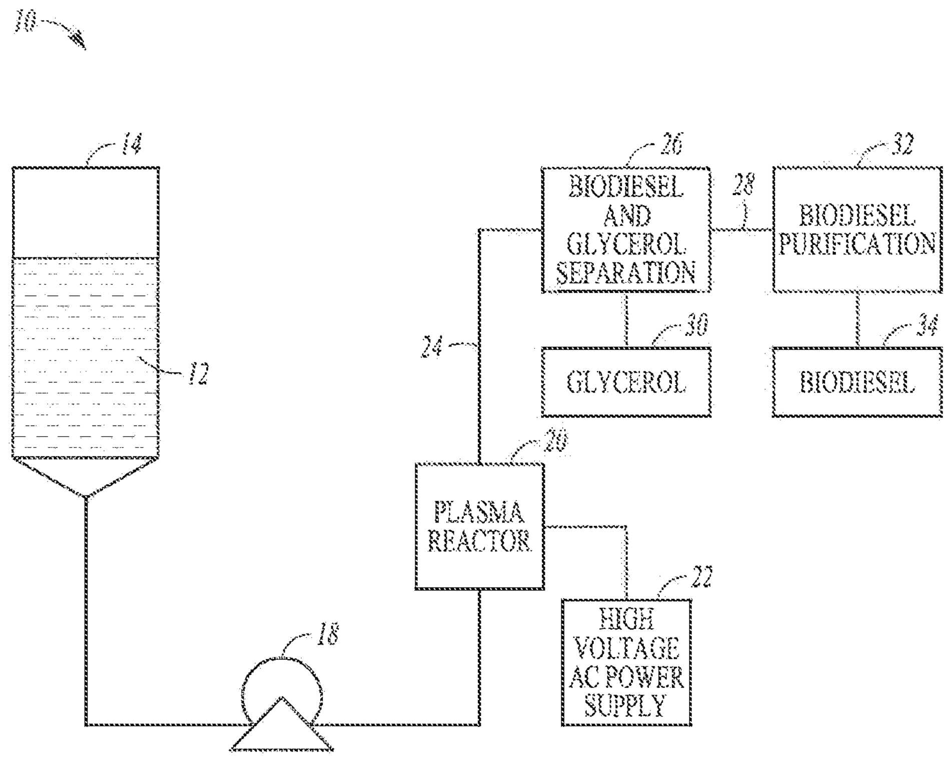
FIG. 1 is a schematic process flow diagram of an example process for the production of biodiesel from a feedstock of one or more lipid-based reactants, such one or both of vegetable oil or animal fats.

The present disclosure describes a process for producing biodiesel from one or more lipid-based reactants, such as one or both of one or more oils or one or more fats, using a reactor capable of generating a liquid plasma discharge into the reactant stream.

The present disclosure describes a plasma reactor for the generation of a stable plasma discharge. In an example, the plasma reactor comprises a housing defining one or more interior chambers, a high-voltage electrode positioned at least partially in or proximate to a first portion of the one or more chambers, a first ground electrode positioned at least partially in or proximate to a second portion of the one or more chambers, wherein the second portion is located on a first side of the high-voltage electrode, a first dielectric plate between the first ground electrode and the high-voltage electrode, the first dielectric plate comprising one or more first openings through which a reaction stream can pass from the first portion to the second portion or from the second portion to the first portion, a feed inlet for feeding the reaction stream into the one or more chambers, and a product outlet for withdrawing the reaction stream from the one or more chambers.

The present disclosure also describes a process for producing a product composition. In an example, the process comprises feeding a reactant stream comprising one or more reactant compounds to a plasma reactor, and discharging a liquid plasma into the reactant stream in the plasma reactor, wherein the liquid plasma initiates or accelerates a reaction of at least one of the one or more reactant compounds to form a product composition. In an example, the plasma reactor used in the process comprises a housing defining one or more interior chambers, a high-voltage electrode positioned at least partially in or proximate to a first portion of the one or more chambers, a first ground electrode positioned at least partially in or proximate to a second portion of the one or more chambers, wherein the second portion is located on a first side of the high-voltage electrode, and a first dielectric plate between the first ground electrode and the high-voltage electrode, the first dielectric plate comprising one or more first openings through which the reactant stream can pass from the first portion to the second portion or from the second portion to the first portion. In such an example, the discharging of the liquid plasma into the reactant stream comprises supplying electrical power to at least the high-voltage electrode such that the liquid plasma is discharged at or proximate to where the reactant stream flows through the one or more first openings.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The example embodiments may be combined, other embodiments may be utilized, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

References in the specification to "one embodiment", "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., at least about 1%, at least about 2%, at least about 3%, and 4%) and the sub-ranges (e.g., 0.1% to 0.5%, at least about 1.1% to 2.2%, at least about 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, at least about 60%, at least about 70%, at least about 80%, at least about 90%, at least about 95%, at least about 96%, at least about 97%, at least about 98%, at least about 99%, at least about 99.5%, at least about 99.9%, at least about 99.99%, or at least about 99.999% or more.

Definitions

It is to be understood that the phraseology or terminology employed herein, and not otherwise defined, is for the purpose of description only and not of limitation. Any use of section headings is intended to aid reading of the document and is not to be interpreted as limiting, and information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety, and wherein the carbon-based moiety can itself be further substituted.

The term "composition" as used herein refers to a chemical, compound, or substance, or a mixture or combination of two or more such chemicals, compounds, or substances.

The term "solvent" as used herein refers to a liquid that can dissolve a solid, another liquid, or a gas. Non-limiting examples of solvents are silicones, organic compounds, water, alcohols, ionic liquids, and supercritical fluids.

The term "room temperature" as used herein refers to a temperature of about 15° C. to about 28° C.

The term "standard temperature and pressure" as used herein refers to 20° C. and 101 kPa.

System for Biodiesel Synthesis

The present disclosure describes various embodiments of a device that discharges liquid plasma for use in the production of biodiesel. The liquid-plasma discharge devices and methods described herein provide for the sustainable production of biodiesel. For example, the liquid-plasma discharge device can provide for an alternating current ("AC")-powered liquid-plasma process. At sufficiently high voltages, e.g., from about 3 kilovolts (kV) to about 30 kV, the energy associated with electric discharge in the reaction stream is sufficient to break down the chemical bond in one or more of oils, fats, or alcohols. In some examples, the generated liquid-plasma induces a transesterification reaction and provides the energy needed for completion of the reaction for biodiesel synthesis. The inventors have discovered that a reaction system including a liquid-plasma discharge device as described herein is able to generate liquid-plasma for successful biodiesel synthesis using an inexpensive and small AC power supply, rather than a high-cost, large-sized pulse power supply. The inventors have also discovered that when a system including a liquid-plasma discharge device as described herein is used, continuous production of high quality biodiesel from renewable oil-containing substrates is possible. The inventors have also discovered that the liquid-plasma discharge technology described herein offers advantages over conventional and other available techniques for biodiesel synthesis including at least one of, and in some examples, all of: enhanced feedstock selectivity, rapid reaction (e.g., at least about 1 second or less), little or no preheating needed, and with significantly reduced needs for separation or purification of the resulting product stream. A process for biodiesel production using a liquid plasma discharged into the reactant mixture as the energy source for the transesterification reaction is also described herein.

As noted above, in some examples, biodiesel is formed by the transesterification of a lipid-based biomass, such as vegetable oil or animal fats, or both. In an example, the lipid-based biomass is reacted with an alcohol, typically methanol ($CH_3OH$), in the presence of a catalyst via the general Reaction [1].

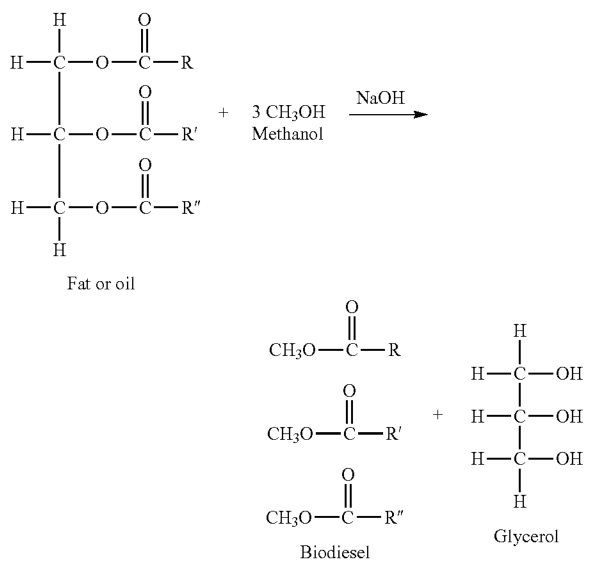

Fat or oil

Biodiesel

Glycerol

FIG. 1 is a schematic flow diagram of an example process 10 for the production of biodiesel using liquid-plasma technology, as summarized above. In an example, the biodiesel production process 10 includes a biomass feedstock 12 that is fed to a reactor 20 that can discharge a stable plasma into the reactant mixture that is fed to the reactor 20. For this reason, the reactor 20 will be referred to hereinafter as a "liquid plasma reactor 20" or simply "plasma reactor 20" for brevity. Examples of the plasma reactor 20 are described in more detail below.

In an example the biomass feedstock 12 is kept in a storage vessel, such as a feedstock tank 14, before it is delivered to the plasma reactor 20. The biomass feedstock 12 can comprise, for example, a lipid-based reactant such as vegetable oil and/or animal fats. For the sake of brevity, the lipid-based reactant may be described herein as "vegetable oil" or simply "oil." However, those with skill in the art will appreciate that the biomass feedstock 12 can comprise one or more animal fats, or a combination of vegetable oil and one or more animal fats.

The one or more lipid-based reactants that are being converted by the plasma reactor 20 are mixed with one or more reactant alcohols, such as methanol (hereinafter referred to simply as "alcohol" for brevity) to form the final biomass feedstock 12. For example, a lipid-based reactant, such as vegetable oil, one or more animal fats, or a combination of vegetable oil and one or more animal fats, can be mixed with one or more reactant alcohols to produce the reactant mixture of the biomass feedstock 12. In the example shown in FIG. 1, the one or more lipid-based reactants and the one or more reactant alcohols are combined in the feedstock tank 14 to form the reactant mixture of the biomass feedstock 12 that is fed to the plasma reactor 20. In some examples, the reactant mixture can include a catalyst, such as catalyst particles mixed in with the lipid-based reactant and the reactant alcohol. However, as described in more detail below, in some examples a catalyst need not be included in the reactant mixture.

Figure 2:
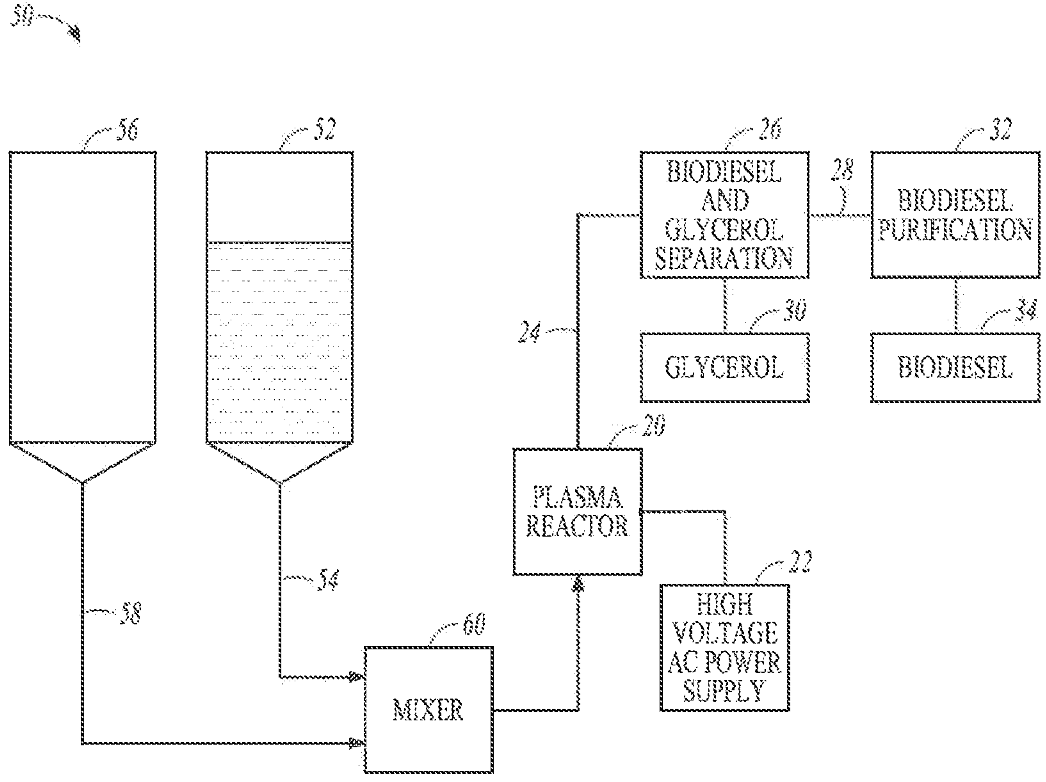
FIG. 2 is a schematic process flow diagram of a second example process for the production of biodiesel from a feedstock of one or more lipid-based reactants.

The reactants need not be mixed together in the same storage vessel, as with the feedstock tank 14 shown in FIG. 1. FIG. 2 shows a schematic flow diagram of an alternative process 50 where the one or more lipid-based reactants and the one or more reactant alcohols are fed to the plasma reactor 20 from separate sources. For example, the one or more lipid-based reactants, such as a feedstock oil, can be stored in an oil storage tank 52 and withdrawn as a lipid-based reactant stream 54 and the one or more reactant alcohols can be kept in an alcohol storage tank 56 and withdrawn as an alcohol stream 58. The lipid-based reactant stream 54 and the alcohol reactant stream 58 can be mixed together with a mixing device 60, referred to simply as a "mixer 60," to form the reactant mixture immediately or substantially immediately before it is fed into the plasma reactor 20. The mixer 60 can be any type of mixing device that is useful for mixing two or more liquid streams together to form a uniform or substantially uniform mixture, particular those that are able to mix the two or more liquid streams as part of a flowing process line (often referred to as an "in-line mixer"). The mixer 60 can be a static mixer or a dynamic mixer. The mixer 60 can also be capable of mixing catalyst particles with the one or more lipid-based reactants and one or more reactant alcohols of the reactant mixture. The catalyst particles can either be previously mixed with one or both of the one or more lipid-based reactants or the one or more reactant alcohols or it can be fed to the mixer 60 separate from the reactant streams In some examples, a mixer like the mixer 60 can be used to mix the reactant mixture even if it is formed upstream of the mixer 60, such as when the lipid-based reactant and the reactant alcohol are initially mixed in the feedstock tank 14. In other words, the mixer 60 can be used to "remix" a previously formed mixture of the reactants. Using a mixing device like the mixer 60 even if the reaction mixture was pre-mixed, such as in a feedstock tank 14, can provide more assurance that the reactant mixture that is fed into the plasma reactor 20 is uniformly or substantially uniformly mixed for more efficient reaction in the plasma reactor 20. The remainder of the process 50 shown in FIG. 2 can be substantially identical to the process 10 of FIG. 1, described in more detail below.

Returning to FIG. 1, in an example, the reactant mixture is delivered to the plasma reactor 20 through a feed line 16 by a feed pump 18. As described in more detail below, in the liquid plasma reactor 20, a plasma is produced and discharged into the liquid of the reactant mixture. The liquid plasma generated by the liquid plasma reactor 20 provides sufficient energy to assist one or more chemical or biological reactions of one or more compounds in the reactant mixture to form a biodiesel product compound. In an example, the liquid plasma generated by the liquid plasma reactor 20 induces, and in some examples provides for the completion of, a transesterification reaction to convert the oil and alcohol to biodiesel, such as the Reaction [1] described above. A power supply 22 provides electrical energy to the plasma reactor 20 in order to drive this plasma formation. In an example, the power supply 22 imposes a relatively high electoral voltage onto the reactant mixture flowing through the plasma reactor 20. Therefore, the power supply 22 will be referred to as a "high-voltage power supply 22," for brevity. In an example, the high-voltage power supply 22 comprises an alternating current ("AC") power supply, and may, therefore, be referred to as the "high-voltage AC power supply 22," in some examples. In an example, the application of a relatively high voltage to the reactant mixture, such as a voltage of at least 2 kilovolts (kV), for example from about 2 kV to about 15 kV or more, allows the plasma reactor 20 to continuously, or substantially continuously, and stably, ro substantially stably, generate a liquid plasma.

The liquid plasma generated by the plasma reactor 20 is discharged into the reactant mixture to form a reaction stream comprising the oil feedstock or some other lipid-based reactant, the reactant alcohol, water, the discharged plasma, and, in some examples, catalyst. In some examples, the reaction stream comprising the lipid-based reactant, the reactant alcohol, and the liquid plasma, is rapidly converted to a product stream comprising a mixture of unconverted reactants (e.g., unconverted oil or alcohol), water, one or more biodiesel compounds (e.g., fatty acid methyl ester, also referred to as "FAME," or other biodiesel ester compounds), and glycerol, where the biodiesel compounds and the glycerol are formed, for example, via Reaction [1]. If a catalyst was included in the reactant mixture mixture, the product stream will also include catalyst. The product stream passes from the plasma reactor 20 through a reactor product line 24 In some examples, this rapid conversion takes place primarily within the plasma reactor 20, i.e., within the housing of the plasma reactor 20 and in close proximity to the electrodes or other structures where the liquid plasma is generated. However, in some examples, at least a portion of the reaction driven by the liquid plasma can occur downstream of the plasma reactor 20 in the reactor product line 24.

The process 10 can include further processing of the product stream to provide a final biodiesel product 34 having desired properties. In an example, the process 10 includes a biodiesel separation system 26 to separate the one or more biodiesel compounds 28 from the other components in the reactor product line 24, such as the glycerol and unconverted reactants 30, referred to simply as a "glycerol stream 30," for brevity. In an example, the one or more separated biodiesel compounds 28 are further processed in a biodiesel purification system 32 to provide the final biodiesel product 34 having a specified purity. The biodiesel separation system 26 can comprise any operation equipment or processes, either known or yet to be known, for separating biodiesel compounds from other compounds, such as those to separated biodiesel compounds from a glycerol stream. Similarly, the biodiesel purification system 32 can comprise any operation equipment or processes, either known or yet to be known, for purifying biodiesel compounds such as the biodiesel compounds 28.

Figure 3:
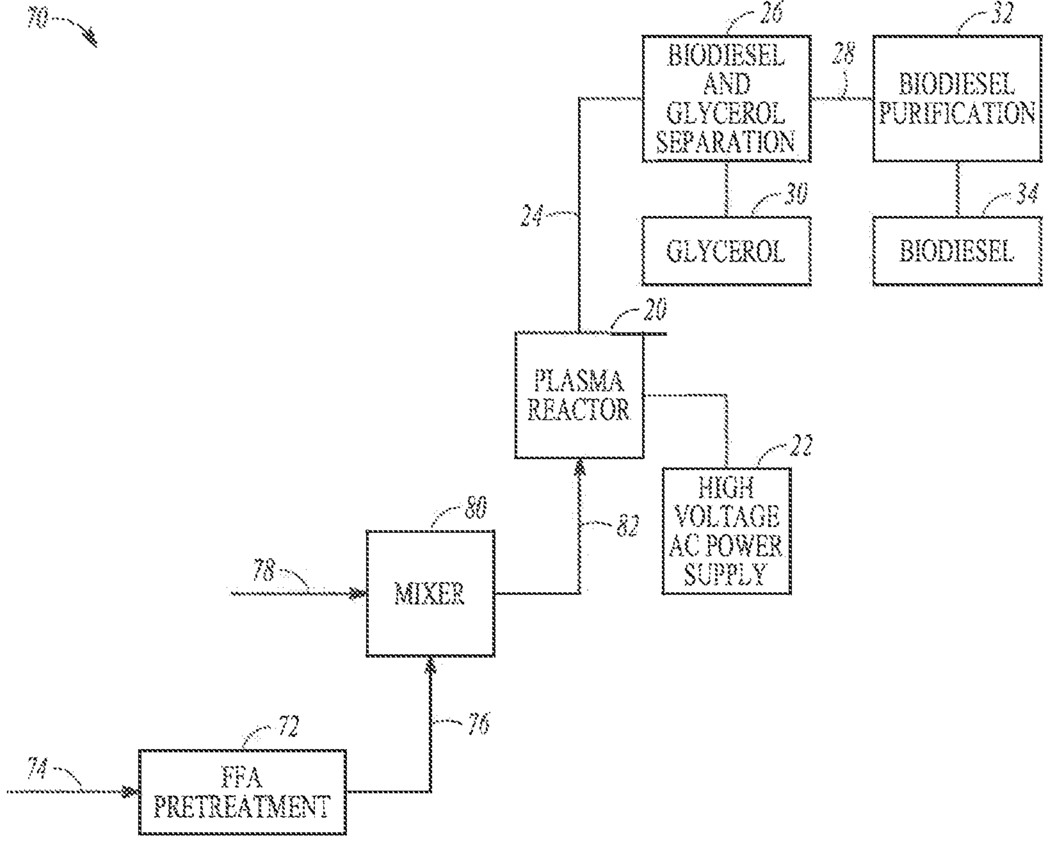
FIG. 3 is a schematic process flow diagram of a third example process or the production of biodiesel from a feedstock of one or more lipid-based reactants.

One or more of the reactants that are fed into the plasma reactor can be pretreated in order to modify one or more of the reactant compounds before they are fed to a reactor. FIG. 3 is a schematic flow diagram of an example process 70 that includes an example of a pretreatment stage 72 that can be included in the process to pretreat a reactant feed stream 74. As will be appreciated by those of skill in the art, FFAs are difficult to process and typically cannot be converted directly to biodiesel compounds such as FAME. The lipid-based reactants that are formed by the conversion of FFAs in the feed stream 74 during the FFA pretreatment 72 combine with other lipid-based reactants that were already in the feed stream 74 to provide a lipid reactant stream 76.

The rest of the process 70 after the FFA pretreatment 72 to provide the lipid reactant stream 76 can be substantially similar to one or more aspects of the process 10 described above with respect to FIG. 1 or the process 50 described above with respect to FIG. 2. For example, the process 70 can include an alcohol reactant stream 78 that comprises one or more reactant alcohols that are to be reacted with one or more lipid-based reactants in the lipid reactant stream 76. The lipid reactant stream 76 and the alcohol reactant stream 78 can be combined with a mixer 80 to uniformly or substantially uniformly mix the one or more lipid-based reactants from the lipid reactant stream 76 and the one or more reactant alcohols from the alcohol reactant stream 78 to provide a reactant mixture in a reactant mixture stream 82. In some examples, the reactant mixture stream 82 can be fed to an optional storage tank (not shown) for storage before it is fed into a plasma reactor 20. In other examples, the reactant mixture stream 82 can be fed directly into the plasma reactor 20. As in the process 10 described above, the plasma reactor 20 is configured to discharge plasma into the reactant mixture from the reactant mixture stream 82 when electricity is supplied to the plasma reactor 20 via a power supply 22. The discharged plasma can initiate, induce, or otherwise assist one or more reactions to convert the lipid-based reactants in the reactant mixture stream 82 to one or more biodiesel compounds in a reaction product stream 24. The reaction product stream 24 can be subjected to further back-end biodiesel processing to provide the final biodiesel product 34, such as one or both of the biodiesel separation system 26 and the biodiesel purification system 32 (described above with respect to FIG. 1).

In an example, the pretreatment stage 72 includes one or more systems or pieces of equipment that are configured to convert free fatty acids (also referred to hereinafter as "FFA" or "FFAs") to one or more lipid-based reactant compounds that can more readily be converted to a desired biodiesel compound, such as FAME. In an example, the pretreatment stage 72 converts FFAs in a lipid-based feedstock in the feed stream 74 to one or more glyceride compounds that will make up the lipid reactant stream 76, such as the triglyceride compound shown as the first reactant in Reaction [1] (labeled as "Fat or oil" in Reaction [1]). A triglyceride compound can be preferable for conversion to biodiesel because, as shown in Reaction [1], each triglyceride compound can produce three different biodisel compounds.

One potential lipid feedstock that is known to have a relatively high proportion of FFAs that has conventionally been difficult to convert to a biodiesel product has been vegetable oils that have been used for food preparation, such as used fry oil, also referred to as "used cooking oil." The FFA pretreatment 72 described above can allow a feedstock that is high in FFAs, like a used cooking oil, to be usable in the process 70 by converting at least a portion of the FFAs to one or more lipid-based reactants that can be converted to one or more biodiesel compounds, such as one or more glyceride compounds that can be converted to one or more biodiesel compounds via a transesterification reaction with one or more reactant alcohols.

The FFA pretreatment 72 can be any chemical processing that can convert at least a portion of the FFAs present in the feed stream 74 to one or more lipid-based reactants that can be more readily converted to one or more biodiesel compounds. As described above, in some examples, a preferred lipid-based reactant that is formed from the FFAs in the FFA pretreatment 72 is a glyceride compounds, and in particular a triglyceride. Examples of methods or processing that can be performed in the FFA pretreatment 72 include, but are not limited to acid-catalyzed esterification or glycerol esterification (also referred to hereinafter as "glycerolysis").

Acid-catalyzed esterification can include reacting the FFAs in the feed stream 74 with methanol in the presence of an acid to produce water and glyceride compounds (e.g., a mixture of monoglycerides, diglycerides, and triglycerides). Acid-catalyzed esterification can provide for a reduction in acid value (AV) of the feed stream 74, which prepares the lipid-based reactants for conversion to biodiesel compounds via transesterification. After the reaction of the acid-catalyzed esterification has completed, the FFA pretreatment 72 can include separation into an organic fraction, e.g., the lipid reactant stream 76, and an aqueous fraction, e.g., water and unreacted methanol. The unreacted methanol from the aqueous fraction can be recycled back to be used as a portion of the methanol for the acid-catalyzed esterification or as at least a portion of the alcohol reactant stream 78.

Glycerolysis can include reacting the FFAs in the feed stream 74 with glycerol to form water and glycerides (e.g., a mixture of monoglycerides, diglycerides, and triglycerides). As the glycerolysis reactions are carried out over time, the resulting reaction mixture can include unreacted FFAs, water, free glycerol, and a mixture of monoglycerides, diglycerides, and triglycerides. The water and the free glycerol can be separated from the monoglycerides, diglycerides, and the triglycerides (referred to collectively herein as "glycerides") to provide a separated glycerol stream and the lipid reactant stream 76. The glycerol in the separated glycerol stream can be recycled back and used as at least a portion of the glycerol for the glycerolysis. In some examples, the glycerolysis can be acid catalyzed or base catalyzed.

Traditionally, liquid plasma has been generated through electric discharge in a gaseous volume. More recently, there has been increasing interest in the study of pulsed-plasma electric discharge in solutions comprising water and organic compounds, which has led to various applications in both industry and academic research. Pulsed plasma discharge in liquid has been shown to be capable of inducing various reactions including the degradation of organic compounds, the destruction of bacteria and viruses, the oxidation of inorganic ions, the synthesis of nanomaterials and polymers, and biomedical engineering applications. The reactions have typically been found to be initiated by the production, via pulsed-electric discharge, of one or more of: various reactive species, UV radiation, shockwaves, high-electric fields, or heat. In addition, the production of localized regions of high temperature and pressure, and the formation of acoustic waves has also been reported. These resulting effects independently or synergistically complete various reactions rapidly and efficiently. However, pulsed-power supplies are expensive, cumbersome to operate, and have high power requirements, Other research has been conducted in the area of biodiesel production under supercritical fluid conditions. For example, non-catalytic production of biodiesel via a supercritical-alcohol transesterification has been demonstrated to be capable of producing high conversions in a relatively short periods of time with little to no need for catalyst separation. The operating temperature of this supercritical process is very high, however (e.g., around 350° C.) and requires a very high pressure, for example as high as 10 megapascals (MPa). Lab-scale microwave and/or ultrasound applications for biodiesel production have also been investigated and have shown the potential to achieve good results compared to conventional homogeneous transesterification techniques. However, there has been skepticism by researchers that microwave or ultrasound technology can be scaled up to large-scale biodiesel production due to low penetration of the microwave or ultrasound energy, limiting the ability for bulk processing.

The liquid-plasma processes 10, 50, and 70 of FIGS. 1-3 can be compared to other high-energy plasma conditions that provide for a direct chemical production of biodiesel. The liquid-plasma processes 10, 50, 708 can produce a high conversion to the final biodiesel product 34 and provide for advantages over conventional biodiesel production methods, such as the homogeneous transesterification techniques described above. In some examples, the advantages over conventional biodiesel production include, but are not limited to, one or more of:

a) Enhanced feedstock selectivity—it has been found that the liquid-plasma process 10 can handle not only virgin vegetable oils but also waste cooking greases and animal fats with high free fatty acid and water content;

b) Continuous processing and small reactor size—the liquid-plasma process 10 can be operated as a continuous process, which allows the plasma reactor 20 to be of a much smaller size compared to what is needed for batch processing (which is common in conventional biodiesel production);

c) Rapid reaction and high conversion rate—the liquid plasma generated in the plasma reactor 20 can release enough energy for the ionization of biological compounds, resulting in substantially higher reaction and conversion rate. For example, it has been found that the plasma reactor 20 in the process 10 of FIG. 1 can achieve reaction to biodiesel compounds in as little as 1 second or less versus as much as 2-4 hours for conventional homogenous transesterification. The reaction rate has even been found to provide for faster reaction and conversion rates than the microwave and ultrasound methods that achieve heat transfer only;

d) Reduced heating requirements—as an energy source, the liquid plasma generated by the plasma reactor 20 produces heat by its interaction with materials at a molecular level, providing energy transfer instead of heat transfer, resulting in more effective and faster heating of catalysts, such that preheating of the reactor bed is substantially reduced, and in some examples, completely eliminated, as opposed to conventional methods that require substantial preheating;

e) Reduced downstream processing requirements—the electrical charges carried due to the plasma discharged by the plasma reactor 20 can greatly accelerate biodiesel and glycerol separation. Moreover, the need for extra alcohol for the transesterification reaction in (or immediately downstream of) the plasma reactor 20 is greatly reduced or even eliminated by the use of liquid plasma, which can greatly reduce or eliminate the requirement for alcohol recycling compared to conventional biodiesel production processes; and f) Improved scalability—stable liquid-plasma discharge by the plasma reactor 20 is achievable with relatively simple reactor designs, as is demonstrated by the example reactor designs shown in FIGS. 2-6 and described below. It is believed that scale-up of the process 10 to large-scale biodiesel production will be readily achievable.

The liquid-plasma processes 10, 50, 70 described herein also have advantages over previous biodiesel-producing methods, such as those described above, including one or more of: lower temperature demands, lower pressure demands, a smaller and simpler design (e.g., reduced device volume), or less sensitivity to contaminants. Finally, the liquid-plasma processes 10, 50, 708 described herein has been found to be able to produce plasma of sufficient energy to drive the transesterification reaction with substantially less energy requirements and with substantially less capital investment compared to other high-energy plasma production (such as the pulsed plasma discharge methods described above) and compared to other high-energy biodiesel production methods (such as the lab-scale microwave or ultrasound methods described above).

The plasma reactor 20 in the processes 10, 50, 70 enables the use of an AC power supply to realize the function of pulse power. As a result, the device volume and operation cost can be substantially reduced. Those having skill in the art will appreciate, however, that direct current ("DC") power or pulse-based power can be used with the plasma reactor 20 and the process 10 described herein, if desired.

At a sufficient supplied electric voltage, a reaction stream with an appropriate combination of reactants, e.g., one or more lipid-based reactants and one or more reactant alcohols for biodiesel production, and in some examples a catalyst, can be processed through the plasma reactor 20. In an example, The electronic voltage supply can be considered to be "sufficient," for the purposes of the plasma reactor 20, if the resulting liquid plasma has sufficient energy to break down one or more chemical bonds of the one or more reactants and/or to form one or more chemical bonds of the one or more product compounds. For example, for biodiesel compounds, in some examples, the electronic voltage can be considered "sufficient" if the liquid plasma energy can break down one or more chemical bonds of the one or more lipid-based reactants and the one or more reactant alcohols in the reactant mixture to induce transesterification or to provide sufficient energy for completion of the transesterification to one or more biodiesel compounds, or both.

In an example, a voltage supply to the plasma reactor 20 that is sufficient for the purposes of the liquid-plasma processes 10, 50, 70, e.g., that is sufficient to break the chemical bonds of the one or more lipid-based reactants and the one or more reactant alcohols to induce a transesterification reaction and to provide enough energy for completion of the reaction to one or more biodiesel compounds, is at least 2 kilovolts (kV), for example from about 2 kV to about 15 kV.

In an example, the voltage supply to the plasma reactor 20 to produce a liquid plasma having sufficient energy for the process 10 is at least about 2 kV, at least about 2.5 kV, at least about 2.6 kV, at least about 2.7 kV, at least about 2.8 kV, at least about 2.9 kV, at least about 3 kV, at least about 3.1 kV, at least about 3.2 kV, at least about 3.3 kV, at least about 3.4 kV, at least about 3.5 kV, at least about 3.6 kV, at least about 3.7 kV, at least about 3.8 kV, at least about 3.9 kV, at least about 4 kV, at least about 4.1 kV, at least about 4.2 kV, at least about 4.3 kV, at least about 4.4 kV, at least about 4.5 kV, at least about 4.6 kV, at least about 4.7 kV, at least about 4.8 kV, at least about 4.9 kV, at least about 5 kV, at least about 5.1 kV, at least about 5.2 kV, at least about 5.3 kV, at least about 5.4 kV, at least about 5.5 kV, at least about 5.6 kV, at least about 5.7 kV, at least about 5.8 kV, at least about 5.9 kV, at least about 6 kV, at least about 6.1 kV, at least about 6.2 kV, at least about 6.3 kV, at least about 6.4 kV, at least about 6.5 kV, at least about 6.6 kV, at least about 6.7 kV, at least about 6.8 kV, at least about 6.9 kV, at least about 7 kV, at least about 7.1 kV, at least about 7.2 kV, at least about 7.3 kV, at least about 7.4 kV, at least about 7.5 kV, at least about 7.6 kV, at least about 7.7 kV, at least about 7.8 kV, at least about 7.9 kV, at least about 8 kV, at least about 8.1 kV, at least about 8.2 kV, at least about 8.3 kV, at least about 8.4 kV, at least about 8.5 kV, at least about 8.6 kV, at least about 8.7 kV, at least about 8.8 kV, at least about 8.9 kV, at least about 9 kV, at least about 9.1 kV, at least about 9.2 kV, at least about 9.3 kV, at least about 9.4 kV, at least about 9.5 kV, at least about 9.6 kV, at least about 9.7 kV, at least about 9.8 kV, at least about 9.9 kV, at least about 10, at least about 10.1 kV, at least about 10.2 kV, at least about 10.3 kV, at least about 10.4 kV, at least about 10.5 kV, at least about 10.6 kV, at least about 10.7 kV, at least about 10.8 kV, at least about 10.9 kV, at least about 11 kV, at least about 11.1 kV, at least about 11.2 kV, at least about 11.3 kV, at least about 11.4 kV, at least about 11.5 kV, at least about 11.6 kV, at least about 11.7 kV, at least about 11.8 kV, at least about 11.9 kV, at least about 12 kV, at least about 12.1 kV, at least about 12.2 kV, at least about 12.3 kV, at least about 12.4 kV, at least about 12.5 kV, at least about 12.6 kV, at least about 12.7 kV, at least about 12.8 kV, at least about 12.9 kV, at least about 13 kV, at least about 13.1 kV, at least about 13.2 kV, at least about 13.3 kV, at least about 13.4 kV, at least about 13.5 kV, at least about 13.6 kV, at least about 13.7 kV, at least about 13.8 kV, at least about 13.9 kV, at least about 14 kV, at least about 14.1 kV, at least about 14.2 kV, at least about 14.3 kV, at least about 14.4 kV, at least about 14.5 kV, at least about 14.6 kV, at least about 14.7 kV, at least about 14.8 kV, at least about 14.9 kV, or at least 15 kV.

The actual voltage that will be sufficient for a particular process 10, 50, 70, e.g., that will be sufficient for transesterification of the one or more lipid-based reactants and the one or more reactant alcohols in the reactant mixture within the plasma reactor 20, can depend on several factors, such as the specific reactant lipid-based reactant or compositions and reactant alcohol or alcohols being used, the specific biodiesel product compound or compounds desired, the concentration of the reactants in the plasma reactor 20, the specific catalyst being used, the loading or concentration of the catalyst in the reactant mixture or in the plasma reactor 20, the operating temperature of the plasma reactor 20 during the reaction, the operating pressure within the plasma reactor during the reaction, and the desired production rate of the process 10, 50, 70.

Liquid Plasma Discharge Reactor

FIGS. 4-9 show various examples of liquid plasma reactor structures that can be used to assist one or more chemical or biological reactions of one or more compounds in a reactant mixture. Each of the example liquid plasma reactor structures in FIGS. 4-9 can, for example, be used as the liquid plasma reactor 20 in the example biodiesel production processes 10, 50, 70 shown in FIGS. 1-3. As is summarized above, the liquid plasma reactor generates electrically-induced liquid plasma that provides energy to drive one or more chemical or biological reactions in order to rapidly convert the one or more reactant compounds in the reactant mixture, such as one or more oils or other lipid-based reactants and one or more reactant alcohols, into one or more biodiesel compounds.

Figure 4:
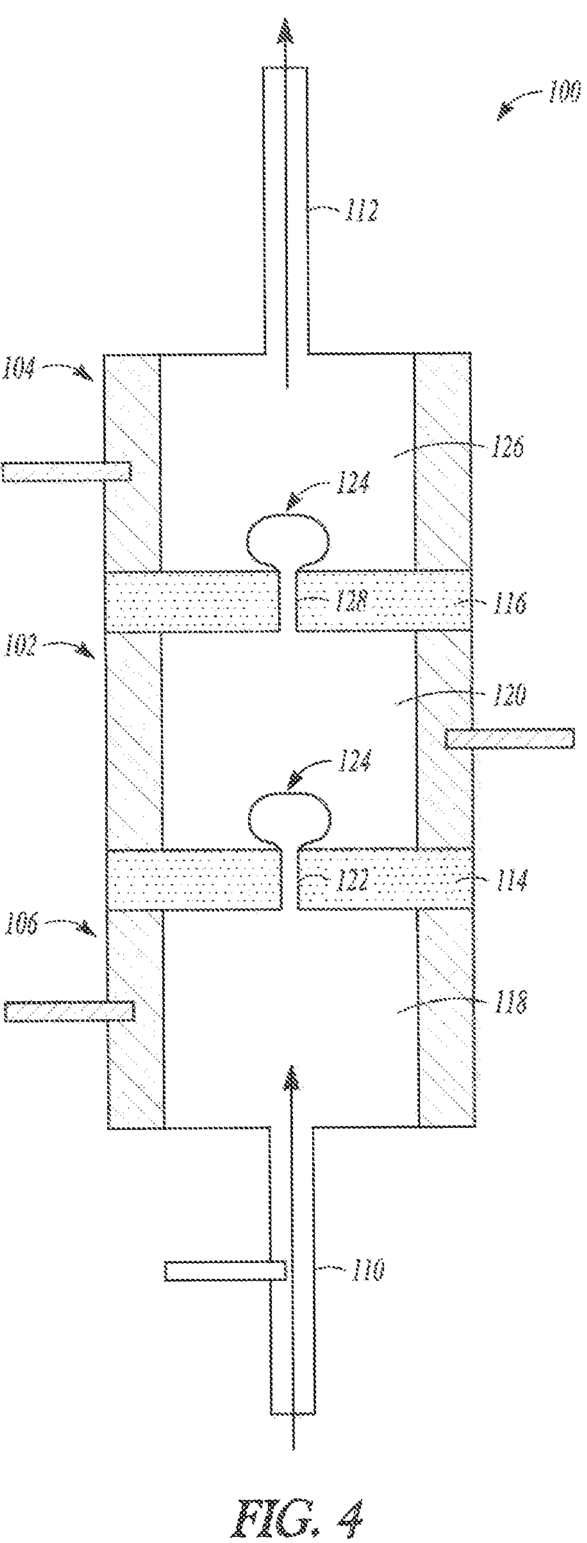
FIG. 4 is conceptual cross-sectional view of an example reactor capable of discharging a liquid plasma into a reactant stream, for example for use in one or more of the processes of FIGS. 1-3.

FIG. 4 is a schematic diagram showing a first example of a liquid plasma reactor 100 configured to generate a liquid plasma discharge into a liquid reaction stream. As discussed above, the liquid plasma has sufficient energy to assist chemical or biological reaction of one or more compounds in the reaction stream. For example, the plasma reactor 100 of FIG. 4 can be used for transesterification of one or more lipid-based reactants and one or more reactant alcohols such that the example liquid plasma reactor 100 shown in FIG. 4 can be used as the plasma reactor 20 in the biodiesel production processes 10, 50, 70 of FIGS. 1-3. In an example, the plasma reactor 100 comprises electrodes 102, 104, 106 that are in contact with a flow path of the reactant mixture that is flowing through the plasma reactor 100. When electrical energy is supplied to one or more of the electrodes 102, 104, 106, e.g., electrical energy from a power supply such as the high-voltage power supply 22 in the process 10 of FIG. 1, liquid plasma is discharged into the flow path so that the liquid plasma mixes with the reactant mixture. In an example, the reactant mixture (e.g., the feedstock mixture of one or more lipid-based reactants and one or more reactant alcohols, as in the processes 10, 50, 70 of FIGS. 1-3) enters the plasma reactor 100 through a feed line 110, and the reaction stream (e.g., discharged liquid plasma and/or transesterification reaction products, unreacted lipid-based reactant, and unreacted reactant alcohol) exits the plasma reactor 100 through an outlet line 112. The plasma reactor 100 is depicted without any catalyst being loaded in the plasma reactor 100. Therefore, the example plasma reactor 100 shown in FIG. 4 can be used in a process where catalyst is included in the reactant mixture, for example with particles of catalyst material being mixed into and entrained within the reactant mixture.

The plasma reactor 100 comprises a high-voltage electrode 102 and one or more ground electrodes 104, 106. In the example depicted in FIG. 4, the high-voltage electrode 102 is positioned longitudinally between a pair of ground electrodes 104, 106. In an example, a first ground electrode 104 is positioned at or proximate to the feed line 110 and a second ground electrode 106 is positioned at or proximate to the outlet line 112. In the example of FIG. 4, the high-voltage electrode 102 and the one or more ground electrodes 104, 106 are tubular or generally tubular in shape so that each electrode 102, 104, 106 surrounds or substantially surrounds a portion of the flow path of the reactant mixture.

In an example, a dielectric structure 114, 116 is positioned between the high-voltage electrode 102 and each of the one or more ground electrodes 104, 106. For example, a first dielectric plate 114 can be positioned between the high-voltage electrode 102 and the first ground electrode 104 so that the first dielectric plate 114 is upstream of the high-voltage electrode 102, and will therefore be referred to as the "upstream dielectric plate 114." A second dielectric plate 116 can be positioned on an opposite side of the high-voltage electrode 102 from the upstream dielectric plate 114 and between the high-voltage electrode 102 and the second ground electrode 106 so that the second dielectric plate 116 is downstream of the high-voltage electrode 102, and will therefore also be referred to as the "downstream dielectric plate 116."

In an example, the reactant mixture passes from the feed line 110 into a lumen 118 that is surrounded or substantially surrounded by the tubular first ground electrode 104A, which will be referred to hereinafter as the "first ground lumen 118." In an example, the first ground lumen 118 is bounded on its sides or periphery by the first ground electrode 104 and at its longitudinal ends by the end of the plasma reactor 100 (e.g., proximate to the feed line 110) and by the upstream dielectric plate 114.

The reactant mixture passes from the first ground lumen 118 into another lumen 120 that is surrounded or substantially surrounded by the tubular high-voltage electrode 102, which will be referred to hereinafter as the "high-voltage lumen 120." In an example, the high-voltage lumen 126 is bounded on its sides or periphery by the high-voltage electrode 102 and at its longitudinal ends by the upstream dielectric plate 114 and the downstream dielectric plate 116. In an example, the reactant mixture passes from the first ground lumen 118 to the high-voltage lumen 120 by passing through one or more openings 122 in the upstream dielectric plate 114. Examples of configurations of the one or more openings 122 include, but are not limited to one or any combination of: one or more perforations in the upstream dielectric plate 114, one or more slits in the upstream dielectric plate 114, one or more holes in the upstream dielectric plate 114, or one or more other types of openings in the upstream dielectric plate 114.

The one or more openings 122 in the upstream dielectric plate 114 cause the flowing reactant mixture to form one or more discharge regions 124 immediately downstream of the upstream dielectric plate 114. The inventors have found that the discharge of liquid plasma can be particularly prevalent in the one or more discharge regions 124. The discharged plasma tends to initiate a transesterificaiton reaction between the reactants in the reactant mixture (e.g., the one or more lipid-based reactants and the one or more reactant alcohols) to produce one or more transesterification reaction products (e.g., one or more biodiesel compounds) that mixes with unreacted reactants from the reactant mixture in the high-voltage lumen 120 to form the reaction stream.

The reaction stream, which now includes the one or more transesterification reaction products produced due to the initiation energy supplied by the discharged liquid plasmas, passes from the high-voltage lumen 120 to another lumen 126 that is surrounded or substantially surrounded by the tubular second ground electrode 106, which is referred to hereinafter as the "second ground lumen 126." In an example, the second ground lumen 126 is bounded on its sides or periphery by the second ground electrode 106 and at its longitudinal ends by the downstream dielectric plate 116 and the end of the plasma reactor 100 (e.g., proximate to the outlet line 112). In an example, the reaction stream passes from the high-voltage lumen 120 to the second ground lumen 126 by passing through one or more openings 128 in the downstream dielectric plate 116. Examples of configurations of the one or more openings 128 include, but are not limited to one or any combination of: one or more perforations in the downstream dielectric plate 116, one or more slits in the downstream dielectric plate 116, one or more holes in the downstream dielectric plate 116, or one or more other types of openings in the downstream dielectric plate 116.

In the example configuration depicted in FIG. 4, each dielectric plate 114, 116 acts not only as a dielectric barrier between the high-voltage electrode 102 a corresponding ground electrode 104, 106, but also acts as a flow barrier to temporarily hinder the flow rate of the reactant mixture or the reaction stream between corresponding adjacent lumens, such as between the first ground lumen 118 and the high-voltage lumen 120 or between the high-voltage lumen 120 and the second ground lumen 126. The reaction stream passes from the second ground lumen 126, and thus out of the plasma reactor 100, through the outlet line 112.

Figure 5:
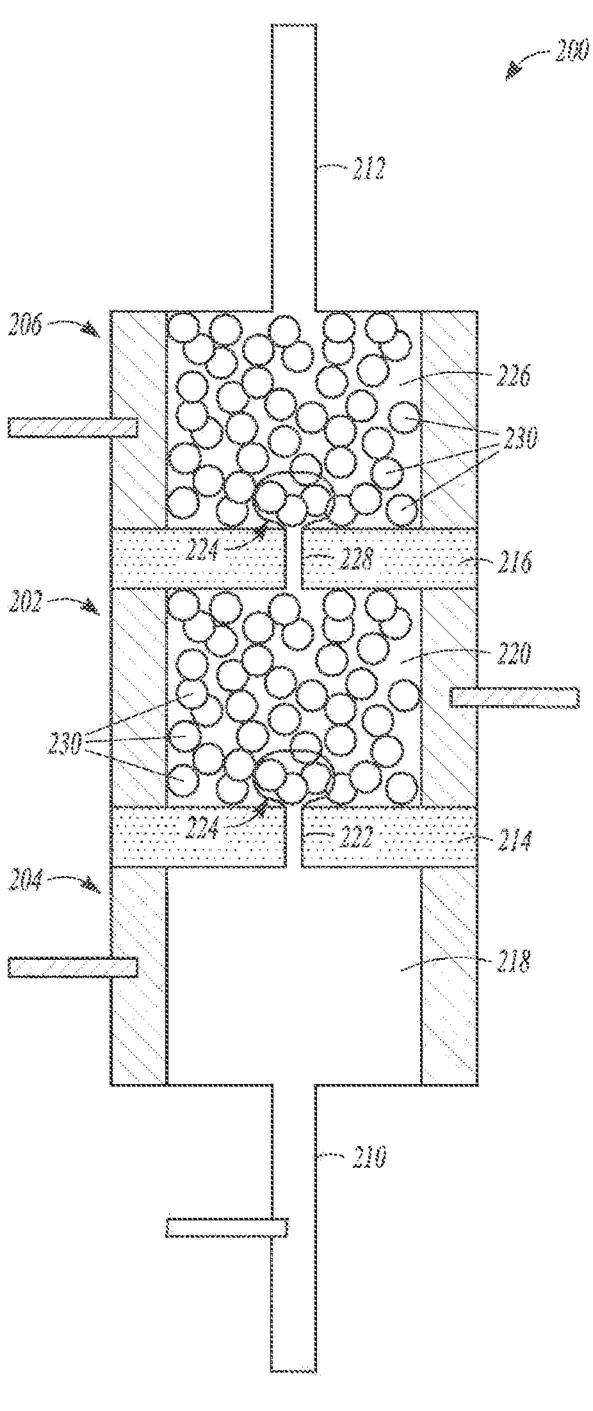
FIG. 5 is a conceptual cross-sectional view of a second example reactor capable of discharging a liquid plasma into a reactant stream, for example for use in one or more of the processes of FIGS. 1-3

FIG. 5 shows a second example liquid plasma reactor 200 capable of generating a liquid plasma discharge into a liquid reactant mixture to assist chemical or biological reaction of one or more compounds in the reactant mixture. In this way the plasma reactor 200, like the plasma reactor 100 shown in FIG. 4, can be used for transesterification of one or more lipid-based reactants and one or more reactant alcohols such that the example liquid plasma reactor 200 shown in FIG. 5 can be used as the plasma reactor 20 in the biodiesel production processes 10, 50, 70 of FIGS. 1-3. The plasma reactor 200 of FIG. 5 is similar to the example plasma reactor 100 depicted in FIG. 4. For example, the plasma reactor 200 includes electrodes 202, 204, 206 that are in contact with a flow path of the reactant mixture through the plasma reactor 200.

Electrical energy suppled to the electrodes 202, 204, 206 causes liquid plasma to be discharged into the flow path so that the liquid path can contact the reactants and initiate or facilitate initiation of a transesterification reaction. In an example, the plasma reactor 200 includes a high-voltage electrode 202 and one or more ground electrodes 204, 206. In an example, the high-voltage electrode 202 is positioned longitudinally between a pair of ground electrodes 204, 206, such as between a first ground electrode 204 positioned at or proximate to a feed line 210 that feeds into the plasma reactor 200 and a second ground electrode 206 positioned at or proximate to an outlet line 212 from the plasma reactor 200. Like the plasma reactor 100 of FIG. 4, in an example, the high-voltage electrode 202 and the one or more ground electrodes 204, 206 are tubular or generally tubular in shape so that each electrode 202, 204, 206 surrounds or substantially surrounds a portion of the flow path of the reactant mixture.

A dielectric structure 214, 216 can be positioned between the high-voltage electrode 202 and each of the one or more ground electrodes 204, 206, such as a first dielectric plate 214 positioned between the first ground electrode 204 and the high-voltage electrode 202 upstream of the high-voltage electrode 202 (referred to as the "upstream dielectric plate 214") and a second dielectric plate 216 positioned between the second ground electrode 206 and the high-voltage electrode 202 downstream of the high-voltage electrode 202 (referred to as the "downstream dielectric plate 216"). The dielectric plates 214, 216 and the vessel of the plasma reactor 200 can act as boundaries to one or more lumens where the reactant mixture or reaction stream flow in the plasma reactor 200. For example, an end of the plasma reactor 200 proximate to the feed line 210 and the upstream dielectric plate 114 are boundaries to a lumen 218 that is surrounded or substantially surrounded by the first ground electrode 204 (referred to as the "first ground lumen 218"), the dielectric plates 214, 216 are boundaries to a lumen 220 that is surrounded or substantially surrounded by the high-voltage electrode 202 (referred to as the "high-voltage lumen 220"), and the downstream dielectric plate 216 and an end of the plasma reactor 200 proximate to the outlet line 212 are boundaries to a lumen 226 that is surrounded or substantially surrounded by the second ground electrode 206 (referred to as the "second ground lumen 226").

In an example, one or more openings 222 are provided in the upstream dielectric plate 214 and one or more openings 228 are provided in the downstream dielectric plate 216. Like the openings 122, 128 in the dielectric plates 114, 116, described above, examples of configurations of the one or more openings 222 in the upstream dielectric plate 214 and the one or more openings 228 in the downstream dielectric plate 216 include, but are not limited to one or any combination of: one or more perforations, one or more slits, one or more holes, or one or more other types of openings in the corresponding dielectric plate 214, 216.

In an example, the reactant mixture flows through the plasma reactor 200 in much the same way it does in the example plasma reactor 100 of FIG. 4. For example, the reactant mixture can flow from the feed line 210 into the first ground lumen 218, then through the one or more openings 222 in the upstream dielectric plate 214 to form one or more discharge regions 224 within the high-voltage lumen 220, and then through the one or more openings 228 in the downstream dielectric plate 216 into the second ground lumen 226, and finally out of the second ground lumen 226 (and, therefore, out of the plasma reactor 200) via the outlet line 212.

The primary difference between the example plasma reactor 200 of FIG. 5 and the plasma reactor 100 of FIG. 4 is that the plasma reactor 200 includes a catalyst 230 loaded in on or more lumens 218, 220, 226 in the plasma reactor 200. In an example, the catalyst 230 comprises a plurality of catalyst particles loaded into the one or more lumens 218, 220, 226, wherein the catalyst particles can comprise particles of catalyst material or particles of a support material to which the catalyst material is coupled.

In an example, the catalyst 230 is loaded at least in the high-voltage lumen 220. In an example, the catalyst 230 is loaded in the high-voltage lumen 220 and in at least one of the ground lumens 218, 226. In an example, the catalyst 230 is loaded in the high-voltage lumen 220 and both of the ground lumens 218, 226 (not shown in FIG. 5). In the example shown in FIG. 5, the catalyst 230 is loaded in the high-voltage lumen 220 and the second ground lumen 226 (e.g., the downstream ground lumen 226, which is depicted as the topmost ground lumen in FIG. 5). The amount of the catalyst 230 that is loaded into the plasma reactor 200 is sufficient for the desired reaction, e.g., the transesterification reaction or reactions to one or more biodiesel product compounds, and to achieve a specified yield within the plasma reactor 200 under the conditions that will be present in the plasma reactor 200. The catalyst 230 loaded in the plasma reactor 200, as depicted in FIG. 5, can be used in place of or in addition to catalyst particles that are mixed within the reactant mixture and fed to the plasma reactor 200 through the feed line 210.

Figure 6:
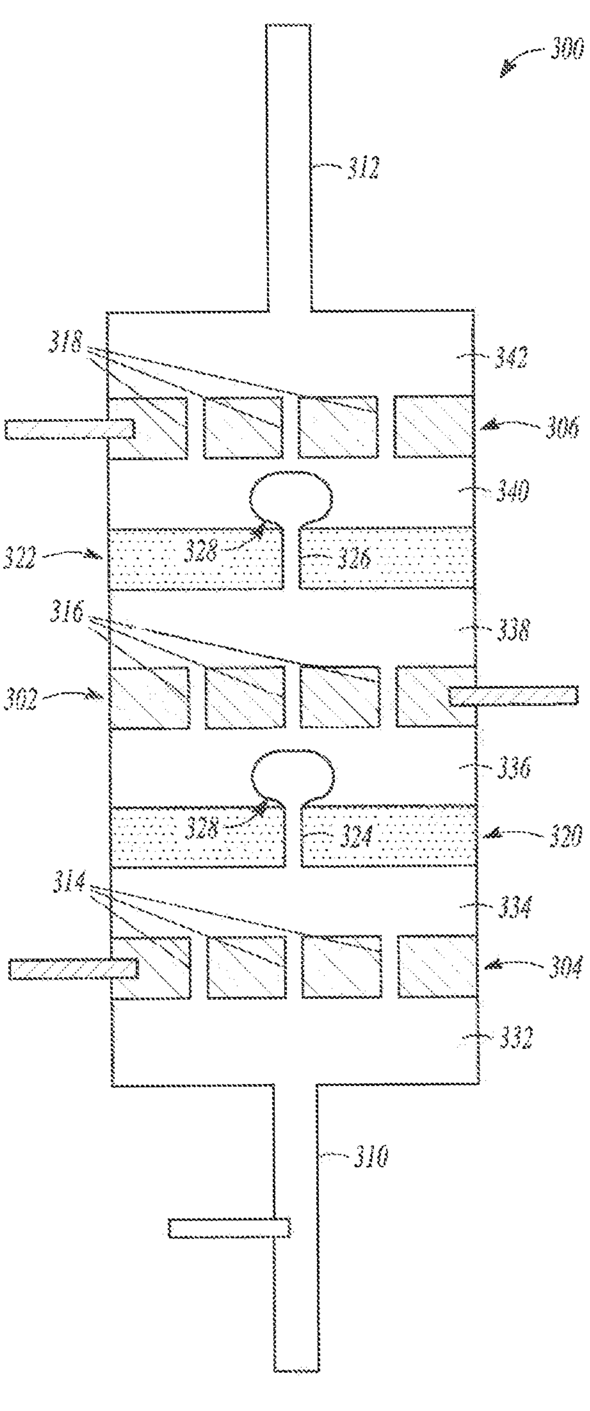
FIG. 6 is a conceptual cross-sectional view of a third example reactor capable of discharging a liquid plasma into a reactant stream, for example for use in one or more of the processes of FIGS. 1-3.

FIG. 6 shows a third example of a liquid plasma reactor 300 capable of generating a liquid plasma discharge into a liquid reactant mixture to assist chemical or biological reaction of one or more compounds in the reactant mixture, for example to assist or facilitate a transesterification reaction of one or more lipid-based reactants and one or more reactant alcohols. Therefore, like the plasma reactors 100 and 200 of FIGS. 2 and 3, the plasma reactor 300 can be used for transesterification of one or more lipid-based reactants and one or more reactant alcohols such that the example liquid plasma reactor 300 shown in FIG. 6 can be used as the plasma reactor 20 in the biodiesel production processes 10, 50, 70 of FIGS. 1-3.

Unlike the example plasma reactors 100 and 200, the example plasma reactor 300 of FIG. 6 uses generally flat, plate-shaped electrodes 302, 304, 206 (hereinafter referred to as "plate electrodes 302, 304, 306" or simply "electrodes 302, 304, 306" for brevity) rather than the tubular or substantially tubular electrodes 102, 104, and 106 and electrodes 202, 204, and 206 described above with respect to the plasma reactors 100 and 200 of FIGS. 4 and 5, respectively. In many other ways, however, the plasma reactor 300 of FIG. 6 is similar to the plasma reactors 100 and 200. For example, electrical energy supplied to the plate electrodes 302, 304, 306 can cause liquid plasma to be discharged into the reactant mixture in the plasma reactor 300, which can initiate or facilitate initiation of a transesterification reaction. In an example, the plasma reactor 300 include a high-voltage plate electrode 302 and one or more ground plate electrodes 304, 306. In an example, the high-voltage plate electrode 302 is positioned longitudinally between a pair of ground plate electrodes 304, 306, such as between a first ground plate electrode 304 positioned at or proximate to a feed line 310 into the plasma reactor 300 and a second ground plate electrode 306 positioned at or proximate to an outlet line 312 from the plasma reactor 300.

In the example depicted in FIG. 6, each plate electrode 302, 304, 306 includes one or more openings through which the reactant mixture can pass as it flows through the plasma reactor 300. For example, one or more openings 314 can pass through the first ground plate electrode 304, one or more openings 316 can pass through the high-voltage plate electrode 302, and one or more openings 318 can pass through the second ground plate electrode 306. Examples of structures that can form any of the openings 314, 316, 318 include, but are not limited to one or any combination of: one or more perforations, one or more slits, one or more holes, or one or more other types of openings in the corresponding plate electrode 302, 304, 306.

In the example, the plasma reactor 300 includes a dielectric structure 320, 322 positioned between the high-voltage plate electrode 302 and each of the one or more ground plate electrodes 304, 306. In an example, each dielectric structure 320, 322 comprises a dielectric plate 320, 322, similar to the dielectric plates 114, 116, 214, 215 in the plasma reactors 100, 200 described above. In an example, a first dielectric plate 320 is positioned between the first ground plate electrode 304 and the high-voltage plate electrode 302 upstream of the high-voltage plate electrode 302 (referred to as the "upstream dielectric plate 320") and a second dielectric plate 322 is positioned between the second ground plate electrode 306 and the high-voltage plate electrode 302 downstream of the high-voltage plate electrode 302 (referred to as the "downstream dielectric plate 322").

In an example, one or more openings 324 are provided in the upstream dielectric plate 320 and one or more openings 326 are provided in the downstream dielectric plate 322, similar to the openings 122, 128, 222, 228 in the dielectric plates 114, 116, 214, 216, respectively, in the example plasma reactors 100, 200 of FIGS. 4 and 5. As with those openings, the one or more openings 324, 326 in the dielectric plates 320, 322 can produce discharge regions 328 immediately downstream of the dielectric plates 320, 322, which the inventors have found can be particularly conducive to plasma discharge. In some examples, the one or more openings 314, 316, 318 in the plate electrodes 302, 304, 306 may generate discharge regions similar to the discharge regions 328 formed by the openings 324, 326 in the dielectric plates 320, 322.

In an example, the reactant mixture is fed through the feed line 310 into a first chamber 332 proximate to the first ground plate electrode 304, referred to herein as the "first inlet ground chamber 332". Next, the reactant mixture passes through the one or more openings 314 in the first ground plate electrode 304 into a second chamber 334 proximate to but on an opposite side of the first ground plate electrode 304 from the first inlet ground chamber 332, referred to hereinafter as the "second inlet ground chamber 334." The reactant mixture then passes through the one or more openings 324 in the upstream dielectric plate 320 into a first chamber 336 proximate to the high-voltage plate electrode 302, referred to hereinafter as the "first high-voltage chamber 336."

Plasma discharge into one or more of the chambers in the plasma reactor 300, such as at least into the first high-voltage chamber 336 or the second high-voltage chamber 338, or both, can induce, initiate, or otherwise assist in reaction of the one or more reactants in the reactant mixture to provide at least one reaction product that mixes with unreacted reactants from the reactant mixture to provide a reaction stream.

From the first high-voltage chamber 336, the reaction stream passes through the one or more openings 316 in the high-voltage plate electrode 302 and into a second chamber 338 proximate to but on an opposite side of the high-voltage plate electrode 302 from the first high-voltage chamber 336, referred to hereinafter as the "second high-voltage chamber 338." The reaction stream then passes through the one or more openings 326 in the downstream dielectric plate 322 into a first chamber 340 proximate to the downstream dielectric plate 322 and the second ground plate electrode 306, referred to hereinafter as the "first outlet ground chamber 340." The reaction stream can then pass through the one or more openings 318 in the second ground plate electrode 306 into a second chamber 342 proximate to but on an opposite side of the second ground plate electrode 306 from the first outlet ground chamber 340, referred to hereinafter as the "second outlet ground chamber 342." From the second outlet ground chamber 342, the reaction stream exits the plasma reactor 300 through the outlet line 312.

The plasma reactor 300 of FIG. 6 can be configured without catalyst being loaded therein (as shown in the example of FIG. 6), or with catalyst loaded into one or more chambers 332, 334, 336, 338, 340, or 342 in the plasma reactor 300, similar to the catalyst loaded in one or more lumens 218, 220, 226 of the example plasma reactor 200 of FIG. 5. In an example, catalyst (e.g. catalyst particles or catalyst loaded on a catalyst support) can be loaded in one or both of the first and second high-voltage chambers 336, 338. In an example, catalyst can be loaded in one or both of the high-voltage chambers 336, 338, in one or both of the inlet ground chambers 332, 334, and one or more of the outlet ground chambers 340, 342. In an example, catalyst can be loaded in one or both of the high-voltage chambers 336, 338 and in one or both of the inlet ground chambers 332, 334 or in one or both of the outlet ground chambers 340, 342 (but not both the inlet ground chambers and the outlet ground chambers).

Figure 7:
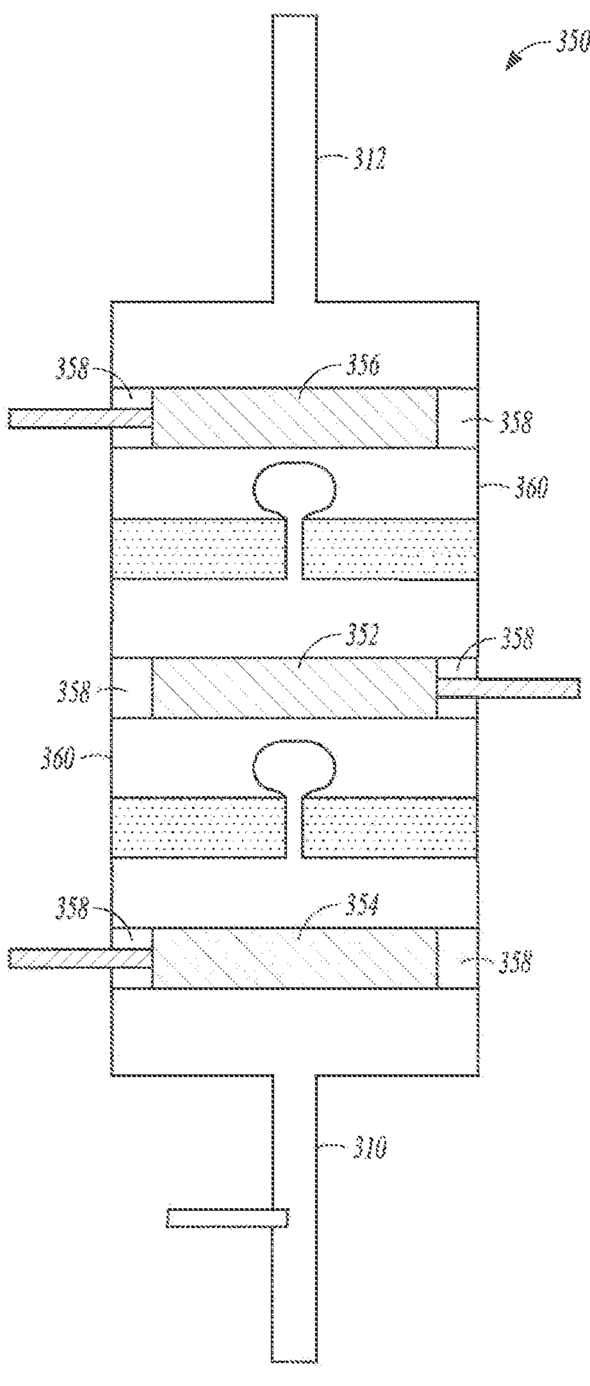
FIG. 7 is a conceptual cross-sectional view of an alternative reactor capable of discharging a liquid plasma into a reactant stream, for example for use in one or more of the processes of FIGS. 1-3, wherein the alternative reactor of FIG. 7 is similar to the third example reactor of FIG. 6, but with a different configuration of one or more electrodes in the reactor another example liquid-plasma generating reactor comprising rod electrodes.

In an alternative example, depicted in FIG. 7 shows an example of a plasma reactor 350 that is substantially similar to the plasma reactor 300 described above with respect to FIG. 6. The plasma reactor 350 include plate electrodes 352, 354 356 that are substantially the same as the plate electrodes 302, 304, 306 (i.e., a high-voltage plate electrode 352 and one or more ground plate electrodes 354, 356), but rather than having the one or more openings 314, 316, 318 as with the plate electrodes 302, 304, 306, one or more of the plate electrodes 352, 354 356 are sized with a cross-sectional area that is smaller than the cross section of the plasma reactor 350 immediately proximate to that particular plate electrode 352, 354 356 such that at least one gap 358 is formed between the plate electrode 352, 354 356 and a wall 360 of the plasma reactor 350 so that a flow path is provided through the plasma reactor 350 for the reactant mixture and the reaction stream around one or more of the plate electrodes 352, 354 356.

Figure 8:
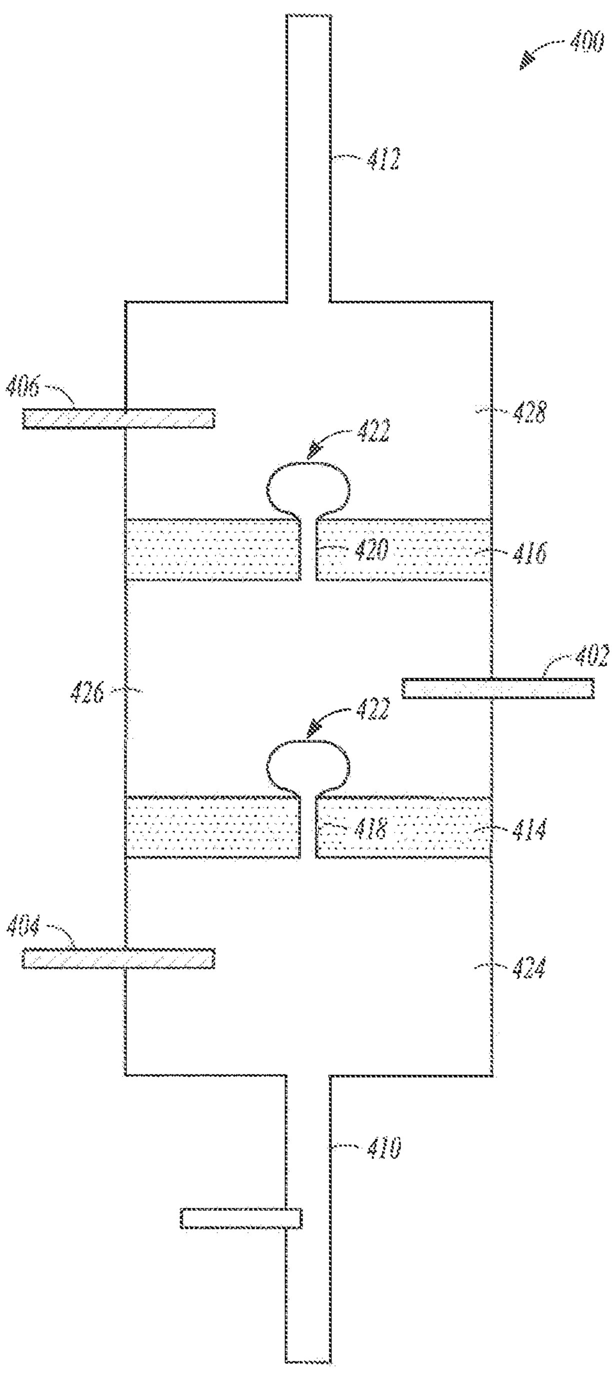
FIG. 8 is a conceptual cross-sectional view of a fourth example reactor capable of discharging a liquid plasma into a reactant stream, for example for use in one or more of the processes of FIGS. 1-3.

FIG. 8 shows a fourth example of a plasma reactor 400 capable of generating a liquid plasma discharge into a liquid reactant mixture to initiate, induce, or otherwise assist chemical or biological reaction of one or more compounds in the reactant mixture, for example for the transesterification of one or more lipid-based reactants and one or more reactant alcohols in the biodiesel production processes 10, 50, 70 of FIGS. 1-3. The example plasma reactor 400 of FIG. 8 uses generally rod-shaped electrodes 402, 404, 406 (referred to as "rod electrodes" hereinafter for brevity) rather than the generally tubular electrodes 102, 104, 106, 202, 204, 206 in the plasma reactors 100 and 200 of FIG. 4 and or the generally flat plate electrodes 302, 304, 306, 352, 354, 356 in the plasma reactors 300 and 350 of FIGS. 6 and 7. In many other ways, however, the plasma reactor 400 of FIG. 8 is similar to the plasma reactors 100, 200, and 300. For example, electrical energy supplied to the rod electrodes 402, 404, 406 can cause liquid plasma to be discharged into the reactant mixture in the plasma reactor 400, which can initiate or facilitate initiation of a transesterification reaction. In an example, the rod electrodes 402, 404, 406 include a high-voltage rod electrode 402 and one or more ground rod electrodes 404, 406, such as a first ground rod electrode 404 proximate to a feed line 410 on a first side of the high-voltage rod electrode 402 and a second ground rod electrodes 404, 406 proximate to an outlet line 412 on a second side of the high-voltage rod electrode 402.

The plasma reactor 400 can include a dielectric structure positioned between at least between the high-voltage rod electrode 402 and each of the one or more ground rod electrodes 404, 406. In an example, each dielectric structure comprises a dielectric plate 414, 416316, similar to the dielectric plates 114, 116, 214, 215 in the plasma reactors 100, 200 described above. In an example, a first dielectric plate 414 is positioned between the first ground rod electrode 404 and the high-voltage rod electrode 402 upstream of the high-voltage rod electrode 402 (referred to as the "upstream dielectric plate 414") and a second dielectric plate 416 is positioned between the second ground rod electrode 406 and the high-voltage rod electrode 402 downstream of the high-voltage rod electrode 402 (referred to as the "downstream dielectric plate 416").

In the example depicted in FIG. 8, each dielectric plate 414, 416 includes one or more openings through which the reactant mixture can pass as it flows through the plasma reactor 300. For example, one or more openings 418 can be provided in the upstream dielectric plate 414 and one or more openings 420 can be provided in the downstream dielectric plate 416, similar to the openings 122, 128, 222, 228, 324, 326 in the dielectric plates 114, 116, 214, 216, 320, 326, respectively, in the example plasma reactors 100, 200, and 300 of FIGS. 4, 5, and 67. As with those openings, the one or more openings 418, 420 in the dielectric plates 414, 416 can produce discharge regions 422 immediately downstream of the dielectric plates 414, 416, which the inventors have found can be particularly conducive to plasma discharge.

In an example, a reactant mixture is fed through the feed line 410 into a first chamber 424 into which the first ground rod electrode 404 at least partially extends, referred to herein as the "inlet ground chamber 424." Next, the reactant mixture passes through the one or more openings 418 in the upstream dielectric plate 414 and into a second chamber 426 into which the high-voltage rod electrode 402 at least partially extends, referred to hereinafter as the "high-voltage chamber 426." The flow of the reactant mixture through the one or more openings 418 produces one or more discharge regions 422 in the high-voltage chamber 426. As described above, the inventors have found that the formation of the one or more discharge regions, such as the discharge regions 422 at the one or more openings 418 in the upstream dielectric plate 414 is particularly conducive to plasma formation and discharge in the plasma reactor 400. The plasma discharge into at least the high-voltage chamber 426 can induce, initiate, or otherwise assist in reaction of the one or more reactants in the reactant mixture to provide at least one reaction product that mixes with unreacted reactants from the reactant mixture to provide a reaction stream. From the high-voltage chamber 426, the reaction stream passes through the one or more openings 420 in the downstream dielectric plate 416 into a third chamber 428 into which the second ground rod electrode 406 at least partially extends, referred to hereinafter as the "outlet ground chamber 428." The reaction stream can then pass from the outlet ground chamber 428 out of the plasma reactor 400 through the plasma reactor 400.

The plasma reactor 400 of FIG. 8 can be configured without catalyst being loaded therein, or with catalyst loaded into one or more of the chambers 424, 426, 428 in the plasma reactor 400, similar to the catalyst loaded in one or more lumens 218, 220, 226 of the example plasma reactor 200 of FIG. 5. In an example, catalyst (e.g. catalyst particles or catalyst loaded on a catalyst support) can be loaded in the high-voltage chamber 426. In an example, catalyst can be loaded into the high-voltage chamber 426, into the inlet ground chamber 424, and into the outlet ground chamber 428. In an example, catalyst can be loaded into the high-voltage chamber 426 and into one of the inlet ground chamber 424 or the outlet ground chamber 428, but not both the inlet ground chamber 424 and the outlet ground chamber 428.

Figure 9:
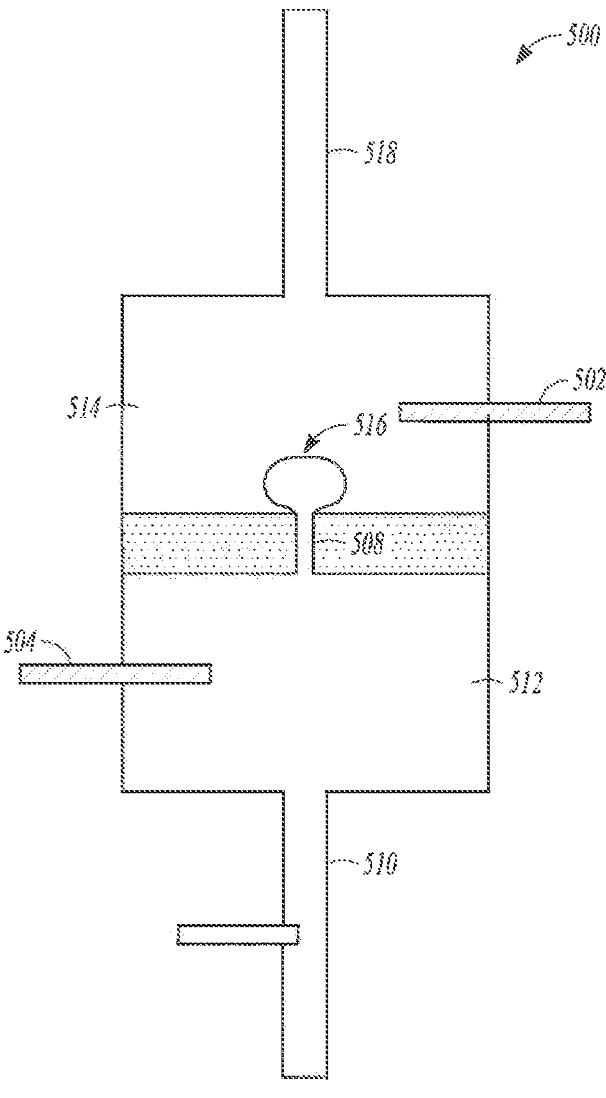
FIG. 9 is a conceptual cross-sectional view of a fifth example reactor capable of discharging a liquid plasma into a reactant stream, for example for use in one or more of the processes of FIGS. 1-3

FIG. 9 shows a fifth example of a plasma reactor 500 that is capable of generating a liquid plasma discharge into a liquid reactant mixture to initiate, induce, or otherwise assist chemical or biological reaction of one or more compounds in the reaction stream, for example for the transesterification of one or more lipid-based reactants and one or more reactant alcohols in the biodiesel production processes 10, 50, 70 of FIGS. 1-3. The example plasma reactor 500 of FIG. 9 is similar to the plasma reactors 100, 200, 300, 350, and 400 of FIGS. 4-8, except that in addition to a high-voltage electrode 502, the plasma reactor 500 includes only a single ground electrode 504 rather than a pair of ground electrodes as in the plasma reactors 100, 200, 300, 350, and 400. Because the plasma reactor 500 only uses a single ground electrode 504, the example plasma reactor 500 of FIG. 9 also comprises only one dielectric structure 506, e.g., a dielectric plate 506, between the high-voltage electrode 502 and the single ground electrode 504. The example plasma reactor 500 shown in FIG. 9 shows the high-voltage electrode 502 and the single ground electrode 504 as being generally rod-shaped electrodes 502, 504. Those of skill in the art will recognize, however, that other forms of electrode can be used for each of the electrodes 502, 504, such as the generally tubular electrode shown in FIGS. 4 and 5 or the generally-plate shaped electrode shown in FIGS. 6 and 7.

The dielectric plate 506 in the plasma reactor 500 is positioned between the high-voltage electrode 502 and the ground electrode 504. In an example, the dielectric plate 506 includes one or more openings 508 to allow fluid to pass through the dielectric plate 506. In an example, a reactant mixture is fed through a feed line 510 into a first chamber 512, which can also be referred to as the "inlet chamber 512." In the example shown in FIG. 9, the inlet chamber 512 is proximate to the ground electrode 504, such as with the generally rod-shaped ground electrode 504 depicted in FIG. 9 being least partially inserted into the inlet chamber 512 (or in which a generally plate-shaped ground electrode could be positioned, or around which a generally tubular-shaped ground electrode could surround. Therefore, in some examples, the first chamber will be referred to as the "ground chamber 512."

Next, the reactant mixture passes through the one or more openings 508 in the dielectric plate 506 and into a second chamber 514. In some examples, the reactant mixture produces one or more discharge regions 516 in the second chamber 514 proximate to the dielectric plate 506 as it flows through the one or more openings 508. As described above, the inventors have found that the formation of the one or more discharge regions, such as the discharge regions 516 at the one or more openings 508 in the dielectric plate 506, is particularly conducive to plasma formation when a sufficiently high voltage is applied to electrodes, such as to the high-voltage electrode 502 and the ground electrode 504. The plasma discharge into second chamber 514 can induce, initiate, or otherwise assist in reaction of the one or more reactants in the reactant mixture to provide at least one reaction product that mixes with unreacted reactants from the reactant mixture to provide a reaction stream. The reaction stream can then exit the plasma reactor 500 via an outlet line 518. For this reason, the second chamber 514 can also be referred to as the outlet chamber 514.

In the example depicted in FIG. 9, the outlet chamber 514 is proximate to the high-voltage electrode 502, so that the outlet chamber 514 can also be referred to as the "high-voltage chamber 514." The example depicted in FIG. 9 shows the inlet chamber 512 as being proximate to the ground electrode 504 and the outlet chamber 514 being proximate to the high-voltage electrode 502, i.e., so that the inlet chamber 512 is a ground chamber 512 and the outlet chamber 514 is a high-voltage chamber 514. In other examples, however, the inlet chamber 512 can be proximate to the high-voltage electrode 502 and the outlet chamber 514 can be proximate to the ground electrode 504 such that the inlet chamber 512 could be considered the high-voltage chamber 512 and the outlet chamber 514 can be considered the ground chamber 514.

The plasma reactor 500 of FIG. 9 can be configured without catalyst loaded therein (as shown in the example of FIG. 9), or with catalyst loaded into one or more of the chambers 512, 514 in the plasma reactor 500, similar to the catalyst loaded in one or more lumens 218, 220, 226 of the example plasma reactor 200 of FIG. 5. In an example, catalyst (e.g. catalyst particles or catalyst loaded on a catalyst support) can be loaded in the high-voltage chamber, whether it is the inlet chamber 512 or the outlet chamber 514. In an example, catalyst can be loaded into the ground chamber, whether it is the inlet chamber 512 or the outlet chamber 514. In an example, catalyst can be loaded into the high-voltage chamber and into the ground chamber, that is into both the inlet chamber 512 and the outlet chamber 514.

Each example reactor of FIGS. 4-9 are shown as comprising the same type of electrode for the high-voltage electrode and the one or more ground electrodes for a particular plasma reactor. However, a person of ordinary skill in the art will appreciate that a combination of two or more electrode types can be used, such as a generally tubular electrode for a first one of the high-voltage electrode, the first ground electrode, and the second ground electrode and either a plate electrode or a rod electrode for a second one of the high-voltage electrode, the first ground electrode, and the second ground electrode. In an example, a third of the high-voltage electrode, the first ground electrode, and the second ground electrode can be the same type as either the first or the second of the high-voltage electrode, the first ground electrode, and the second ground electrode. In an example, the electrodes that have the same type can be the first and second ground electrodes, while the high-voltage electrode is of a different type. In an example, the high-voltage electrode and one of the ground electrodes can be of the same type with the other ground electrode being of a different type. In another example, the third of the high-voltage electrode, the first ground electrode, and the second ground electrode can be of a different type from each of the other two electrodes. A person of skill in the art will also appreciate that generally tubular electrodes, generally flat or generally plate-shaped electrodes, and generally rod-shaped electrodes such as those described above are merely three potential examples of electrode structures that can be used in the plasma reactors and systems of the present invention. Other types and structures of electrodes can easily be contemplated by those of skill in the art.

Reactions Types for the Plasma Reactor

Each of the example plasma reactors 100, 200, 300, 350, 400, and 500 shown in and described with respect to FIGS. 4-9 were primarily described in reference to their use in producing a liquid plasma in order to induce or assist in reactions for producing one or more biodiesel compounds to produce a biodiesel product, for example to induce or assist a transesterification reaction to convert one or more lipid-based reactants and one or more reactant alcohols to one or more biodiesel compounds as in the processes 10, 50, and 70 of FIGS. 1-3. However, the plasma reactors and overall processes of the present invention are not so limited. Rather, a plasma reactor according to the present invention, including the example plasma reactors 100, 200, 300, 350, 400, and 500, can be used for any reaction that can be initiated, induced, or otherwise assisted by the presence of liquid plasma that is produced by the plasma reactor according to the invention.

For example, the plasma reactors can be used for other organic-based reactions, including, but not limited to, polymerization reactions or reactions for the conversion to or from organic compounds including, but not limited to: alkanes, alkenes, alkynes, alcohols, polyols (such as diols or triols and higher order polyols), carboxylic acids, acid anhydrides, acyl halides, acyloins, alkyl halides, alkyl nitrites, amides, amines, imines, arenes, azides, aziridines, cyclopropanes, azo compounds, diazo compounds, ethers, esters, ketones (such as haloketones), cyanates, isocyanates, lactones, lactams, saccharides (including simply sugars, oligosaccharrides, polysaccharides, and starches), nitriles, nitro compounds, phenols, polyphenols (including bisphenols and higher order polyphenols), or thiols. The plasma reactors of the present invention may also be useful for non-organic reactions that can be initiated, induced, or otherwise assisted by the energy input from a plasma that is discharged by the plasma reactor.

Moreover, while plasma reactors according to the present invention can be particularly useful for reactions that take place in a liquid or solution phase because, as described above, the plasma reactors of the present invention are particularly configured to discharge a plasma into a liquid-based reactant mixture. However, the plasma reactors described herein can also be used for reactions in other phases.

For example, the liquid plasma reactors of the present invention can be configured for a reaction where one or more reactants is a solid, but where the one or more solid reactants can be entrained (as small particles), dissolved or dissociated, partially dissolved or dissociated, or dispersed (either colloidally or non-colloidally) in a liquid carrier stream. Similarly, the liquid plasma reactors of the present invention can be configured for a reaction of one or more reactants that are typically in the gaseous phase, wherein the one or more gaseous reactants can be entrained (e.g., as small gas bubbles), dissolved, or partially dissolved, or dispersed (colloidally or non-colloidally) in a liquid carrier stream. Moreover, the liquid carrier stream that is carrier one or both of the one or more solid reactants or one or more gaseous reactants can itself include one or more liquid reactants or one or more solution-based reactants. The discharge of plasma into the liquid carrier stream by the plasma reactors of the present invention can initiate, induce, or otherwise assist reaction and conversion of the one or more solid reactants being carried by the liquid carrier stream, one or more gaseous reactants being carried by the liquid carrier stream, or both.

In some examples, one or more of the plasma reactors of the present invention may also be able to provide for the reaction of one or more reactants that are in the gaseous phase, such as where the reactant mixture is a gaseous stream or primarily a gaseous stream rather than the liquid or solution-based reactant mixtures that are primarily described above.

Operating Conditions of Plasma Reactor

The operation of each of the example plasma reactors 100, 200, 300, 350, 400, and 500 of FIGS. 4-9 can be controlled based on the composition of the reactant mixture, such as the specific compounds being used for the feedstock (e.g., the compositional makeup of the one or more lipid-based reactants and one or more reactant alcohols being converted to biodiesel) and the desired product capacities. In an example, parameters of the plasma reactor 20, such as any of the example plasma reactors 100, 200, 300, 350, 400, or 500 of FIGS. 4-9) that can be modified and controlled include, but are not limited to:

a) A flow rate of the reactant mixture/reaction stream through the plasma reactor—in some examples, the flow rate of the reactant mixture/reaction stream can be scalable based on a desired process capacity;

b) An AC power voltage applied to the plasma reactor—in some examples, the AC power voltage can be selected within a range of from about 110 V to about 30,000 V;

c) A power frequency of the electricity supplied to the plasma reactor—in some examples, the power frequency can be selected within a range of from about 10 Hz to about 15,000 Hz;

d) A treatment time, which can be defined as the residence time of the reactant mixture or reaction stream passing through a discharge region, e.g., the one or more discharge regions 124, 224, 328, 422 from the dielectric structures (e.g., dielectric plates) or an electrode (e.g., plate electrodes) in the plasma reactor. Alternatively the treatment time can be defined as the time that the reactant mixture/reaction stream experiences in the plasma reactor (e.g., a residence time within the plasma reactor), which can be defined either by the residence time within the entire plasma reactor, meaning in all chambers or lumens of the plasma reactor, or it can be defined as a residence time within a specific portion of the plasma reactor's volume, such as the volume associated with the high-voltage electrode (e.g., one or more high-voltage lumens or chambers) or the volume associated with the high-voltage chamber and one or more of the ground electrodes. In an example, the treatment time can be selected within a range of from about 10 microseconds (μS) to about 10 minutes;

e) A thickness of each dielectric structure within the plasma reactor, i.e., a thickness of a dielectric plate, where "thickness" is defined as a distance as measured by drawing a line between a high-voltage electrode and a ground electrode that passes through the dielectric structure. In some examples, the dielectric structure thickness can be selected to be from about 1 millimeter (mm) to about 100 mm;

f) A number of openings in each dielectric structure—in some examples, each dielectric structure (i.e., each dielectric plate) can have between one opening and 50 openings, such as from 1 to 25 openings, for example 1 to 10 openings;

g) The cross-sectional size of each of the openings in the dielectric structure—in an example, the diameter of each opening in the dielectric plate (if the openings have a generally circular cross section) can be from about 0.1 mm to about 100 mm. In the case of non-circular openings, a cross-sectional area that substantially corresponds to the cross-sectional area of generally circular openings having a diameter of from about 0.1 mm to about 100 mm.

EXAMPLE

Various embodiments of the present invention can be better understood by reference to the following Example which is offered by way of illustration. The present invention is not limited to the Example given herein.

A vegetable oil feedstock was mixed with methanol and fed into the example rod electrode plasma reactor described with respect to FIG. 8. The vegetable oil feedstock was continuously fed to the plasma reaction with a pump and piping according to the process flow diagram of FIG. 1.

In the plasma reactor, the high-voltage rod electrode was connected to an AC power supply and a voltage and frequency was set by the control module. Alkaline or acid catalyst (concentration: 0-1 mole/mole) was dissolved in alcohol (e.g., one or more of methanol, ethanol, etc.), and the alcohol-catalyst solution was added to an oil substrate with an alcohol-to-oil molar ratio of 3:1-12:1. The mixture was stirred to a full blend and pumped through the plasma reactor. When the alcohol-oil mixture passed through the discharge regions, which are the holes on the two dielectric plates in the plasma reactor, the plasma discharge occurred. When necessary, air or different gases were introduced into the plasma reactor to form gas bubbles in the reaction stream through a gas inlet. The air or other gasses help plasma generation more easily and save electrical energy by reducing the required discharge voltage.

When plasma discharge is generated in the alcohol-oil liquid mixture, the transesterification reaction is induced. The reaction occurs within 10 μs to 10 minutes. Passing the plasma discharge zone, the alcohol-oil mixture continues to downstream treatment for separation and purification.

The resulting biodiesel was tested by an independent third-party test lab. Table 1 shows some quality data of the plasma-synthesized biodiesel.

TABLE 1

Quality Data of Synthesized Biodiesel

| Parameter | Value | ASTM Standard Test Method |
|---|---|---|
| API Gravity | 28.4 | D288 |
| Cloud Point | +27° F. | D2500 |
| Water Karl Fischer | 670 ppm | D6304 |
| Oxidation Stability | >12 | EN15751 |
| Free Glycerin | 0.003% | D6584 |
| Total Glycerin | 0.082% | D6584 |
| Total Acid Number | 0.42 | D664 |

The terms and expressions that have been employed are used as terms of description and not of limitation, and there is no intention in the use of such terms and expressions of excluding any equivalents of the features shown and described or portions thereof, but it is recognized that various modifications are possible. Thus, it should be understood that although specific embodiments are described herein with reference to optional features, modification and variation of the concepts described herein may be resorted to by those of ordinary skill in the art, and that such modifications and variations are considered to be within the scope of embodiments of the present invention.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method comprising:

feeding a liquid reactant stream comprising one or more reactant compounds to an operating plasma reactor under an operating pressure to continuously, or substantially continuously, and stably, or substantially stably, generate a liquid plasma; and discharging electricity into the liquid reactant stream as it is fed through the operating plasma reactor under the operating pressure to generate the liquid plasma to initiate or accelerate a reaction of at least one of the one or more reactant compounds to form a product composition.

2. The method of claim 1, wherein the one or more reactant compounds include esters, alcohol, acid, water, triglycerides, or a lipid-based or petroleum compounds.

3. The method of claim 1, wherein the reactant stream includes at least one of a lipid-based or petroleum reactant, reactant acid, or a reactant alcohol.

4. The method of claim 1, wherein the reactant stream is converted to the product composition comprising a mixture of unconverted reactants from the reactant stream.

5. The method of claim 4, wherein the unconverted reactants includes unconverted oil, alcohol, water, or glycerol.

6. The method of claim 1, wherein the product composition includes fatty acid ester.

7. The method of claim 1, wherein the reaction that is initiated or accelerated is a transesterification reaction between at least one lipid-based or petroleum compound and at least one alcohol.

8. The method of claim 7, wherein the at least one lipid-based compound includes oil, fat, or a combination of oil and fat.

9. The method of claim 1, wherein the reaction that is initiated or accelerated is an esterification reaction between at least one acid and at least one alcohol.

10. The method of claim 1, further comprising loading a catalyst for the reaction into the operating plasma reactor.

11. The method of claim 1, wherein the plasma initiates or accelerates a reaction causing destruction of bacteria, viruses, and biological organism.

12. The method of claim 1, wherein the plasma initiates or accelerates a reaction causing a break down of one or more chemical bonds of the one or more reactant compounds in the liquid reactant stream.

13. The method of claim 1, wherein the product composition includes water after destruction of bacteria, viruses, and biological organism.

14. The method of claim 1, wherein the reactant compounds initiate or accelerate break down of one or more chemical bonds of a compound in the liquid reactant stream after discharge from the operating plasma reactor.

15. The method of claim 1, wherein the reactant compounds maintain its characteristics to initiate or accelerate the destruction of bacteria, viruses, and biological organism after discharge from the operating plasma reactor.

16. The method of claim 1, wherein feeding the liquid reactant stream to the operating plasma reactor includes delivering a liquid feed to a feed inlet of the operating plasma reactor to form the liquid reactant stream.

17. The method of claim 1, wherein converting the liquid reactant stream to a plasma state that initiates or accelerates the reaction of at least one of the one or more reactant compounds to form the product composition further comprises:

delivering the reactant stream to a high-voltage electrode positioned at least partially in or proximate to a first portion of one or more chambers of a housing of the operating plasma reactor, delivering the reactant stream past a first ground electrode positioned at least partially in or proximate to a second portion of the one or more chambers and proximate to a feed inlet of the operating plasma reactor, wherein the second portion is located on a first side of the high-voltage electrode;

delivering the reactant stream to a second ground electrode positioned at least partially in or proximate to a third portion in the one or more chambers and proximate to a product outlet from the operating plasma reactor, wherein the third portion is located on a second side of the high-voltage electrode that is opposite the first side of the high-voltage electrode, wherein a first dielectric plate is arranged between the first ground electrode and the high-voltage electrode and having one or more first openings through which the liquid reaction stream can pass from the first portion to the second portion or from the second portion to the first portion, and wherein a second dielectric plate positioned between the second ground electrode and the high-voltage electrode and having one or more second openings through which the liquid reaction stream can pass from the first portion to the third portion.

18. The method of claim 17, further comprising suppling electrical power to the high-voltage electrode to discharge a plasma at or proximate to where the reactant stream flows through the one of more first openings and the one of more second openings.

19. The method of claim 18, further comprising controlling connection of the high-voltage electrode to one of an alternating current power supply, a direct current power supply, or a pulse power supply to supply the electrical power to the high-voltage electrode.

20. The method of claim 17, further comprising feeding the liquid reaction stream from the feed inlet to the second portion of the one or more chambers and withdrawing the liquid reaction stream from the third portion of the one or more chambers.

21. The method of claim 1, wherein the reaction stream facilitates one or more polymerization reactions.

22. The method of claim 1, wherein the parameters selected to initiate or accelerate a reaction of at least one of the one or more reactant compounds to form a product composition include at least one of:

an alternating current (AC) power;

a voltage within a range of from about 110 V to about 30,000 V; or a frequency within a range of from about 10 Hz to about 15,000 Hz.

* * * * *